United States Patent
Aotsuka et al.

(10) Patent No.: US 7,115,623 B2
(45) Date of Patent: Oct. 3, 2006

(54) PDE IV INHIBITORS

(75) Inventors: Tomoji Aotsuka, Hamura (JP);
Kentarou Kumazawa, Hamura (JP);
Nagatoshi Wagatsuma, Hamura (JP);
Kouki Ishitani, Hamura (JP); Takashi Nose, Hamura (JP)

(73) Assignee: Aska Pharmaceuticals Co., Ltd., Tokyo (JP)

( * ) Notice: Subject to any disclaimer, the term of this patent is extended or adjusted under 35 U.S.C. 154(b) by 194 days.

(21) Appl. No.: 10/480,378

(22) PCT Filed: Jun. 11, 2002

(86) PCT No.: PCT/JP02/05804

§ 371 (c)(1),
(2), (4) Date: Dec. 11, 2003

(87) PCT Pub. No.: WO02/100859

PCT Pub. Date: Dec. 19, 2002

(65) Prior Publication Data

US 2004/0176365 A1   Sep. 9, 2004

(30) Foreign Application Priority Data

Jun. 12, 2001   (JP) ............................. 2001-176550

(51) Int. Cl.
*C07D 471/02*   (2006.01)
*A61K 31/44*   (2006.01)

(52) U.S. Cl. ...................... 514/300; 546/113
(58) Field of Classification Search ............... 546/113; 514/300

See application file for complete search history.

(56) References Cited

U.S. PATENT DOCUMENTS

| | | | |
|---|---|---|---|
| 4,452,800 A | 6/1984 | Sherlock | 31/435 |
| 4,786,642 A | 11/1988 | Teulon | 514/300 |
| 5,817,670 A | 10/1998 | Takayama et al. | 514/300 |
| 6,642,250 B1 * | 11/2003 | Aotsuka et al. | 514/300 |

FOREIGN PATENT DOCUMENTS

| | | |
|---|---|---|
| JP | 62-228076 | 6/1987 |
| WO | 96/06843 | 7/1996 |
| WO | 01/42244 | 6/2001 |

OTHER PUBLICATIONS

STN pp. (7).*

* cited by examiner

*Primary Examiner*—Zinna N. Davis
(74) *Attorney, Agent, or Firm*—Wenderoth, Lind & Ponack, L.L.P.

(57) ABSTRACT

The purpose is to provide selective PDE IV inhibitors which have a potent anti-asthmatic profile with excellent safety. A compound of the formula (1):

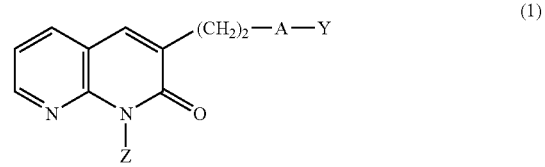

wherein A is methylene, lower alkylmethylene, carbonyl, etc., Y is a 5- or 6-membered heteroaryl group containing one or two heteroatoms selected from nitrogen, sulfur and oxygen, Z is i) a fused ring in which any of 5- or 6-membered heteroaryl groups is fused to a benzene ring, or ii) a phenyl group which may be unsubstituted or optionally substituted with one or more members selected from the group consisting of nitro, amino, an amino nitrogen-containing group, etc., provided that when A is methylene, Y is a 5- or 6-membered heteroaryl group selected from the group consisting of pyrrolyl, pyridyl, etc., and Z is a phenyl group which may be unsubstituted or substituted, the substituent on said phenyl group is amino, or an amino nitrogen-containing group; or a pharmaceutically acceptable salt thereof, possesses excellent PDE IV inhibition and is useful as a pharmaceutical drug, preferably an anti-asthmatic, etc.

13 Claims, No Drawings

PDE IV INHIBITORS

This application is a U.S. national stage of International Application No. PCT/JP02/05804 filed Jun. 11, 2002.

FIELD OF THE INVENTION

The present invention relates to novel 1,8-naphthyridin-2(1H)-one derivatives that inhibit phosphodiesterase (hereinafter, referred to as "PDE") IV, or pharmaceutically acceptable salts thereof, and to pharmaceutical compositions comprising the same.

BACKGROUND OF THE INVENTION

PDEs are enzymes which hydrolyze intracellular cyclic AMP (cAMP) and intracellular cyclic GMP (cGMP) and widely distributed in vivo in various tissues and organs. Up to now, it has been known that PDEs are classified into 7 isoenzyme families, i.e., type I to VII PDEs (PDE I to VII), according to their properties. Among them, PDE IV is known to be an enzyme which is predominantly present in airway smooth muscle cells and a wide variety of inflammatory cells, i.e., neutrophils, eosinophils, lymphocytes, etc. and selectively breaks down cAMP. In addition, it has been known that an elevation of cAMP levels in airway smooth muscle cells leads to relaxation of the airway smooth muscles. An increase of cAMP levels in inflammatory cells has also been known to suppress an activation of inflammatory cells, including, for example, a release of cytotoxic proteins from eosinophils, etc.

Therefore, if PDE IV predominantly located in airway smooth muscle cells and inflammatory cells is inhibited by inhibitors selective for said isozyme form, an elevation of cAMP levels would be induced in such cells. As a result, it would be expected to elicit bronchodilator actions via relaxing airway smooth muscles and anti-inflammatory actions through suppressing inflammatory cell activation. Such selective inhibitors of PDE IV would be expected to become excellent anti-asthmatic agents and therapeutic agents for chronic obstructive pulmonary disease (COPD).

Up to now, it has been known that a xanthine derivative theophylline, a catechol derivative rolipram, and the like, are inhibitors of PDE IV. Theophylline inhibits PDE in various tissues due to its non-selectivity for individual isozymes, thereby exerting not only a bronchodilator activity to be targeted but also extra actions on heart, CNS, etc. Although rolipram is observed to be selective for PDE IV, it is easily transferred into the CNS due to its property of being absorbed. Therefore, rolipram has a drawback that it has adverse central side-effects effects such as an emetic action.

Over the past decade, many pharmaceutical companies have focused on the inhibition of PDE IV for the treatment of asthma. The biological studies on the PDE IV isozyme and the structure-activity relationship of said inhibitors have recently been reviewed in the literature. In such processes, it has been pointed out that in general the therapeutic utility of selective PDE IV inhibitors, such as the prototypical agent rolipram, have been hampered by nausea and emesis limiting their therapeutic potential (J. Med. Chem., 41: 2268 to 2277 (1998)).

Under these circumstances, in order to find out pharmaceutical drugs having an excellent anti-asthmatic efficacy via minimizing undesirable side-effects in tissues and organs other than bronchial smooth muscles and inflammatory cells, various PDE IV inhibitors have been screened and examined.

For instance, with an aim at inhibitors with improved selectivity for PDE IV, various compounds including diazepinoindoles (JP, A, 10-507447 (1998)), tri-substituted phenyl derivatives (JP, A, 10-504530 (1998), JP, A, 10-503174 (1998), JP, A, 10-503173 (1998), etc.), naphthalene derivatives (JP, A, 10-226647 (1998)), etc., have been proposed.

Besides these, for the purpose of developing not only anti-asthmatics but also pharmaceutical agents for preventing and treating a wide range for diseases, PDE IV-inhibitory compounds having a naphthyridine ring have been proposed in JP, A, 7-10875 (1995); WO 96/6843, A1; JP, A, 11-106385 (1999); etc.

Such compound groups are, however, unsatisfactory in view of solving the aforementioned problems. There is still a demand for anti-asthmatics which exert more selective PDE IV-inhibiting actions and have advantageous properties from aspects regarding both of efficacy and safety.

SUMMARY OF THE INVENTION

The present inventors have conducted an extensive research on various compounds in order to solve the above problems. As a result, the present inventors have succeeded in producing 1,8-naphthyridin-2(1H)-one derivatives having a 5- or 6-membered heteroaryl group, or a fused benzene ring in which any of the heteroaryl groups is fused to a benzene ring, via 1 to 8 methylene chains on the position 3 of the 1,8-naphthyridin-2(1H)-one nucleus, which exert selective inhibition against PDE IV, and filed a patent application for such compounds (PCT/JP00/08671 (WO 01/42244, A1); hereinafter, referred to as "our filed patent application"). The present inventors have further conducted an extensive research on various compounds based on our findings for said leading compounds covered by our filed patent application. As a result, the present inventors have also succeeded in finding unique 1,8-naphthyridin-2(1H)-one derivatives, found that these novel compounds are not only unexpectedly advantageous over the conventional PDE IV inhibitors but also qualified as potent inhibitors of PDE IV from aspects of pharmacological action and safety, and that intermediate compounds for the production of said specific PDE IV inhibitor compounds can be produced via novel processes, and thus succeeded in accomplishing this invention.

The present invention, as described hereinbelow, encompasses 1,8-naphthyridin-2(1H)-one derivative compounds having a heteroaryl group via an unsubstituted or optionally substituted propylene group, on the position 3 of the 1,8-naphthyridin-2(1H)-one nucleus.

The present invention provides the following:
1) A compound of the formula (1):

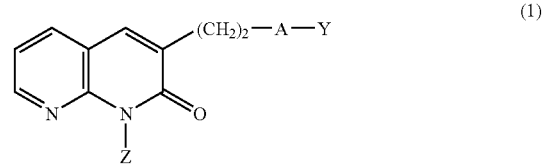

wherein:
A is methylene, lower alkylmethylene, carbonyl, hydroxymethylene or lower alkylcarbonyloxymethylene,
Y is a 5- or 6-membered heteroaryl group containing one or two ring heteroatoms selected from nitrogen, sulfur and oxygen,
Z is
  i) a fused ring in which any of 5- or 6-membered heteroaryl groups is fused to a benzene ring, or
  ii) a phenyl group which may be unsubstituted or optionally substituted with one or more members selected from the group consisting of halogen, cyano, nitro, lower alkylthio, lower alkylsulfinyl, lower alkylsulfonyl, lower alkyl, trifluoromethyl, hydroxyl, lower alkoxy, a residue derived from a carboxylic acid or a derivative thereof, amino, and an amino nitrogen-containing group, provided that when A is methylene, Y is a 5- or 6-membered heteroaryl group selected from the group consisting of pyrrolyl, pyridyl, 1-oxypyridyl, thienyl, furyl, imidazolyl, thiazolyl, and oxazolyl, and Z is a phenyl group which may be unsubstituted or substituted, the substituent on said phenyl group is amino, or an amino nitrogen-containing group;

or a pharmaceutically acceptable salt thereof.

2) The compound according to the above 1), wherein A is methylene, and Z is a fused ring in which any of 5- or 6-membered heteroaryl groups is fused to a benzene ring; or a pharmaceutically acceptable salt thereof.

3) The compound according to the above 1), wherein A is methylene, and Y is a 6-membered heteroaryl group containing two nitrogen atoms in the ring; or a pharmaceutically acceptable salt thereof.

4) The compound according to the above 1), wherein A is methylene, and Y is pyridyl or 1-oxypyridyl, Z is a phenyl group substituted with amino or an amino nitrogen-containing group; or a pharmaceutically acceptable salt thereof.

5) The compound according to the above 1), wherein A is lower alkylmethylene, and Z is a phenyl group which may be unsubstituted or optionally substituted with one or more members selected from the group consisting of halogen, cyano, nitro, lower alkylthio, lower alkylsulfinyl, lower alkylsulfonyl, lower alkyl, trifluoromethyl, hydroxyl, lower alkoxy, a residue derived from a carboxylic acid or a derivative thereof, amino, and an amino nitrogen-containing group; or a pharmaceutically acceptable salt thereof.

6) The compound according to the above 1), wherein A is carbonyl, and Z is a phenyl group which may be unsubstituted or optionally substituted with one or more members selected from the group consisting of halogen, cyano, nitro, lower alkylthio, lower alkylsulfinyl, lower alkylsulfonyl, lower alkyl, trifluoromethyl, hydroxyl, lower alkoxy, a residue derived from a carboxylic acid or a derivative thereof, amino, and an amino nitrogen-containing group; or a pharmaceutically acceptable salt thereof.

7) The compound according to the above 1), wherein A is hydroxymethylene, and Z is a phenyl group which may be unsubstituted or optionally substituted with one or more members selected from the group consisting of halogen, cyano, nitro, lower alkylthio, lower alkylsulfinyl, lower alkylsulfonyl, lower alkyl, trifluoromethyl, hydroxyl, lower alkoxy, a residue derived from a carboxylic acid or a derivative thereof, amino, and an amino nitrogen-containing group; or a pharmaceutically acceptable salt thereof.

8) The compound according to the above 1), wherein A is lower alkylcarbonyloxymethylene, and Z is a phenyl group which may be unsubstituted or optionally substituted with one or more members selected from the group consisting of halogen, cyano, nitro, lower alkylthio, lower alkylsulfinyl, lower alkylsulfonyl, lower alkyl, trifluoromethyl, hydroxyl, lower alkoxy, a residue derived from a carboxylic acid or a derivative thereof, amino, and an amino nitrogen-containing group; or a pharmaceutically acceptable salt thereof.

9) The compound according to the above 2), wherein Y is pyridyl or 1-oxypyridyl; or a pharmaceutically acceptable salt thereof.

10) The compound according to the above 3), wherein Z is a phenyl group which may be unsubstituted or optionally substituted with one or more members selected from the group consisting of halogen, cyano, nitro, lower alkylthio, lower alkylsulfinyl, lower alkylsulfonyl, lower alkyl, trifluoromethyl, hydroxyl, lower alkoxy, a residue derived from a carboxylic acid or a derivative thereof, amino, and an amino nitrogen-containing group; or a pharmaceutically acceptable salt thereof.

11) The compound according to any of the above 5) to 8), wherein Z is a phenyl group which is substituted with one or more members selected from the group consisting of nitro, amino, and an amino nitrogen-containing group, and Y is pyridyl or 1-oxypyridyl; or a pharmaceutically acceptable salt thereof.

12) 1-(3-Aminophenyl)-3-[3-(pyridin-4-yl)propyl]-1,8-naphthyridin-2(1H)-one.

13) 1-(3-Aminophenyl)-3-[3-(1-oxypyridin-4-yl)propyl]-1,8-naphthyridin-2(1H)-one.

14) 1-(3-Nitrophenyl)-3-[3-methyl-3-(pyridin-4-yl)propyl]-1,8-naphthyridin-2(1H)-one.

15) 1-(3-Nitrophenyl)-3-[3-methyl-3-(1-oxypyridin-4-yl)propyl]-1,8-naphthyridin-2(1H)-one.

16) 1-(3-Nitrophenyl)-3-[3-oxo-3-(pyridin-4-yl)propyl]-1,8-naphthyridin-2(1H)-one.

17) 1-(3-Nitrophenyl)-3-[3-hydroxy-3-(pyridin-4-yl)propyl]-1,8-naphthyridin-2(1H)-one.

18) A pharmaceutical composition which comprises an effective amount of a compound according to any of the above 1) to 17) or a pharmaceutically acceptable salt thereof in admixture with a pharmaceutically acceptable carrier.

19) A phosphodiesterase IV inhibitor comprising an effective amount of a compound according to any of the above 1) to 17) or a pharmaceutically acceptable salt thereof.

20) An anti-asthmatic comprising an effective amount of a compound according to any of the above 1) to 17) or a pharmaceutically acceptable salt thereof.

21) A drug for the prophylaxis and/or treatment of at least one member selected from diseases or abnormal conditions related to phosphodiesterase IV activity, said drug comprising an effective amount of a compound according to any of the above 1) to 17) or a pharmaceutically acceptable salt thereof.

22) A drug comprising an effective amount of a compound according to any of the above 1) to 17) or a pharmaceutically acceptable salt thereof, said drug for preventing and/or treating at least one disease or abnormal condition selected from the group consisting of:

(1) respiratory diseases, including bronchial asthma (including chronic bronchial asthma and atopic asthma), acute bronchitis, chronic bronchitis, asthmatic bronchitis, pneumonic diseases, pulmonary emphysema, chronic obstructive pulmonary disease (COPD), acute respiratory distress syndrome (ARDS), and the like;

(2) inflammatory diseases, including atopic dermatitis, conjunctivitis, urticaria, acquired immunodeficiency syndrome (AIDS), keloid formation, rhinitis, iridocyclitis, gingivitis, periodontitis, dentoalveolitis, gastritis, ulcerative colitis, Crohn's disease, gastrointestinal ulcer, esophagitis, myositis, encephalitis (such as myasthenia gravis, multiple sclerosis and neuritis), hepatitis, scar tissue formation, nephritis (including proliferative nephritis), peritonitis, pleurisy, scleritis, scieroderma, scalds or burns, and the like;

(3) systemic or local joint diseases, including osteoarthritis, gouty arthritis, rheumatoid arthritis, malignant rheumatism, psoriatic arthritis, and the like;

(4) inflammatory conditions associated with organ transplantation, etc., including reperfusion injury, graft versus host reaction, and the like;

(5) diseases related to urination, including diabetes insipidus, urethritis, urinary incontinence, cystitis, irritable bladder, neurogenic bladder, uremia, uriniferous tubular disorder, pollakiuria, ischuria, and the like;

(6) diseases or abnormal conditions related to tumor necrosis factor (TNF) (for example, TNF-α, etc.) and other cytokines (for example, IL-1, IL-4, IL-6, etc.), including psoriasis, rheumatoid arthritis, ulcerative colitis, Crohn's disease, septicemia, septic shock, endotoxic shock, gram negative bacillus sepsis, toxic shock syndrome, nephritis, hepatitis, infection (induced by bacteria and viruses), circulatory failure (heart failure, arteriosclerosis, myocardial infarction, cerebral apoplexy), and the like;

(7) proliferative diseases, including malignant tumors, leukemia, proliferative dermal diseases (keratosis and various types of dermatitides), connective tissue diseases and the like;

(8) diseases related to nervous function abnormality, including impaired learning, memory and recognition related to neurodegenerative disorders such as Alzheimer's disease and Parkinson's disease, multiple lateral sclerosis, senile dementia, amyotrophic lateral sclerosis, acute demyelinating neuritis, muscular dystrophy, and the like;

(9) diseases related to abnormality of mental functions, including manic-depressive psychosis, schizoid, anxiety, panic, and the like;

(10) diseases demanding protection of nerves and cells, including cardiac arrest, spinal cord injury, intermittent claudication, ischemic diseases (including angina pectoris, cardiac infarction, cerebral apoplexy, head injury, etc.) and the like;

(11) endocrine diseases, including not only diabetes but also diabetic retinopathy, diabetic nephropathy, diabetic neurosis, amyloidosis, pancreatitis, thyroiditis, obesity, prostatomegaly, and the like;

(12) autoimmune diseases, including systemic lupus erythematosus (SLE), atrophic gastritis, thyroid diseases, glomerular nephritis, orchitis, adrenal diseases, hemolytic anemia, oophoritis, and the like;

(13) cardiovascular diseases, including hypertension, angina pectoris, heart failure, myocarditis, external epicarditis, endocarditis, valvulitis, and the like;

(14) vessel and blood system diseases, including anguitis, aneurysm, endoangiosis, thromboangiitis, granulomatosis, cerebrovascular angiitis, arteriosclerosis, periangitis, leukopenia, thrombocytopenia, Boeck's sarcoid, and the like;

(15) diseases related to immune reactions or allergic responses, including contact dermatitis, serum sickness, drug allergy, Goodpasture's syndrome, lymphoma, rheumatic fever, AIDS, anaphylactic shock and the like; and

(16) other diseases, disorders or abnormal states, including glaucoma, spastic paralysis, impotence, diseases or illness accompanied with pain (contusion, headache, etc.), neck-shoulder-arm syndrome, nephropathy, renal insufficiency, hepatic insufficiency, obesity, infertility, etc.

23) A drug or agent comprising an effective amount of a compound according to any of the above 1) to 17) or a pharmaceutically acceptable salt thereof, said drug and agent for preventing and/or treating at least one respiratory disease selected from the group consisting of bronchial asthma including chronic bronchial asthma and atopic asthma; acute bronchitis; chronic bronchitis; asthmatic bronchitis; pneumonic diseases; pulmonary emphysema; chronic obstructive pulmonary disease (COPD); and acute respiratory distress syndrome (ARDS).

24) A process for the production of an intermediate for the production of a compound (1) according to the above 1), i.e., a compound having the following general formula (2):

wherein Z has the same meaning as defined above, which comprises reacting 2-bromonicotinaldehyde with a compound having the formula:

$ZNH_2$ wherein Z has the same meaning as defined above.

The above objectives and other objectives, features, advantages, and aspects of the present invention are readily apparent to those skilled in the art from the following disclosures. It should be understood, however, that the description of the specification including the following best modes of carrying out the invention, examples, etc. is illustrating preferred embodiments of the present invention and given only for explanation thereof. It will become apparent to the skilled in the art that a great number of variations and/or alterations (or modifications) of this invention may be made based on knowledge from the disclosure in the following parts and other parts of the specification without departing from the spirit and scope thereof as disclosed herein. All of the patent publications and reference documents cited herein for illustrative purposes are hereby incorporated by reference into the present disclosure.

BEST MODES OF CARRYING OUT THE INVENTION

The present invention provides 1,8-naphthyridin-2(1H)-one derivatives, or salts thereof, having a heteroaryl group via an unsubstituted or optionally substituted propylene group on the position 3 of the 1,8-naphthyridin-2(1H)-one ring, which possess advantageous biological properties, and pharmaceutical compositions comprising at least one member selected from the aforementioned compounds and pharmaceutically acceptable salts thereof. The compounds or salts thereof are utilizable for their selective PDE IV-inhibiting actions. Therefore, the present invention also provides drugs for preventing and/or treating at least one member selected from diseases, disorders, and abnormal conditions related to an activity of PDE IV.

A preferred embodiment of the present invention is as follows:

The definitions for the compounds of the above-defined formula (1) will be given below in detail.

As used herein, the term "lower alkylmethylene" refers to a methylene radical linked to an alkyl radical containing 1 to 4 carbon atoms. Examples of said lower alkylmethylene are methylmethylene, ethylmethylene, propylmethylene, isopropylmethylene, n-butylmethylene, i-butylmethylene, and t-butylmethylene.

The term "lower alkylcarbonyloxymethylene" refers to a methylene radical linked to an alkylcarbonyloxy radical containing 2 to 5 carbon atoms. Examples of said lower alkylcarbonyloxymethylene are acetoxymethylene, ethylcarbonyloxymethylene, propylcarbonyloxymethylene, isopropylcarbonyloxymethylene, n-butylcarbonyloxymethylene, i-butylcarbonyloxymethylene, and t-butylcarbonyloxymethylene.

Representatives of the "5- or 6-membered heteroaryl group containing one or two ring heteroatoms selected from nitrogen, sulfur and oxygen" include pyrrolyl, pyridyl, 1-oxypyridyl, thienyl, furyl, imidazolyl, thiazolyl, oxazolyl, pyrazinyl, pyrimidinyl, pyridazinyl, etc. Among them, preferred groups include pyridyl, 1-oxypyridyl, pyrimidinyl, pyridazinyl, and pyrazinyl. Particularly, pyridyl and 1-oxypyridyl are preferable.

As used herein, the "fused ring in which any of 5- or 6-membered heteroaryl groups is fused to a benzene ring" includes a fused ring in which any of 5-membered heteroaryl groups each containing 1 to 3 heteroatoms selected from nitrogen, sulfur and oxygen is fused to a benzene ring. Examples of the fused ring are benzothienyl, benzofuranyl, indolyl, benzimidazolyl, benzothiazolyl, benzisoxazolyl, benzothiadiazolyl, benzoxadiazolyl, oxy-benzoxadiazolyl, quinolyl, isoquinolyl, quinoxalyl, etc. Among them, preferred rings include benzothiadiazolyl, benzoxadiazolyl, and oxy-benzoxadiazolyl.

The term "halogen" as used herein refers to fluorine, chlorine, bromine, and the like.

The term "lower alkylthio" refers to an alkylthio radical containing 1 to 4 carbon atoms, such as methylthio, ethylthio, propylthio, isopropylthio, n-butylthio, i-butylthio and t-butylthio.

The term "lower alkylsulfinyl" refers to an alkylsulfinyl radical containing 1 to 4 carbon atoms, such as methylsulfinyl, ethylsulfinyl, propylsulfinyl, isopropylsulfinyl, n-butylsulfinyl, i-butylsulfinyl and t-butylsulfinyl.

The term "lower alkylsulfonyl" refers to an alkylsulfonyl radical containing 1 to 4 carbon atoms, such as methylsulfonyl, ethylsulfonyl, propylsulfonyl, isopropylsulfonyl, n-butylsulfonyl, i-butylsulfonyl, and t-butylsulfonyl.

The term "lower alkyl" refers to an alkyl radical containing 1 to 4 carbon atoms, such as methyl, ethyl, propyl, isopropyl, n-butyl, i-butyl, and t-butyl.

The term "lower alkoxy" refers to an alkoxy radical containing 1 to 4 carbon atoms, such as methoxy, ethoxy, propoxy, isopropoxy, n-butoxy, i-butoxy, and t-butoxy.

As used herein, the term "residue derived from a carboxylic acid or a derivative thereof" refers to a carboxylic acid residue, a carbamoyl group, a carboxylic acid lower alkyl ester residue, etc. Examples of such carboxylic acid lower alkyl ester residues are a methyl carboxylate residue, an ethyl carboxylate residue, a propyl carboxylate residue, an isopropyl carboxylate residue, an n-butyl carboxylate residue, an i-butyl carboxylate residue, a t-butyl carboxylate residue, etc.

The term "amino nitrogen-containing group" includes mono- or di-lower alkylamino, carbamoylamino, lower alkylcarbonylamino, etc. Examples of said mono- or di-lower alkylamino groups are mono- or di-methylamino, mono- or di-ethylamino, mono- or di-propylamino, mono- or di-isopropylamino, mono- or di-n-butylamino, mono- or di-i-butylamino, mono- or di-t-butylamino, etc. Examples of said lower alkylcarbonylamino groups are acetylamino, ethylcarbonylamino, propylcarbonylamino, isopropylcarbonylamino, etc.

The "6-membered heteroaryl group containing two ring nitrogen atoms" refers to pyrimidinyl, pyridazinyl, and pyrazinyl.

Preferred compounds according to the present invention have the structural formula (1). More preferred compounds of the structural formula (1) are those in which Y is pyridyl or 1-oxypyridyl. When Z is a phenyl group which may be unsubstituted or substituted for the structural formula (1), the substituent on said phenyl group is preferably nitro, amino, or an amino nitrogen-containing group.

Representative examples of compounds of the invention include the following:

1-(2,1,3-Benzothiadiazol-5-yl)-3-[3-(pyridin-2-yl)propyl]-1,8-naphthyridin-2(1H)-one 1-(2,1,3-Benzothiadiazol-5-yl)-3-[3-(pyridin-3-yl)propyl]-1,8-naphthyridin-2(1H)-one 1-(2,1,3-Benzothiadiazol-5-yl)-3-[3-(pyridin-4-yl)propyl]-1,8-naphthyridin-2(1H)-one 1-(3-Nitrophenyl)-3-[3-(pyrimidin-5-yl)propyl]-1,8-naphthyridin-2(1H)-one 1-(3-Nitrophenyl)-3-[3-(pyridazin-3-yl)propyl]-1,8-naphthyridin-2(1H)-one 1-(3-Nitrophenyl)-3-[3-(pyrazin-2-yl)propyl]-1,8-naphthyridin-2(1H)-one 1-(3-Aminophenyl)-3-[3-(pyridin-4-yl)propyl]-1,8-naphthyridin-2(1H)-one 1-(3-Aminophenyl)-3-[3-(1-oxypyridin-4-yl)propyl]-1,8-naphthyridin-2(1H)-one 1-(3-Dimethylaminophenyl)-3-[3-(pyridin-4-yl)propyl]-1,8-naphthyridin-2(1H)-one.

1-(3-Acetylaminophenyl)-3-[3-(pyridin-4-yl)propyl]-1,8-naphthyridin-2(1H)-one 1-(3-Nitrophenyl)-3-[3-methyl-3-(pyridin-4-yl)propyl]-1,8-naphthyridin-2(1H)-one 1-(3-Nitrophenyl)-3-[3-methyl-3-(1-oxypyridin-4-yl)propyl]-1,8-naphthyridin-2(1H)-one 1-(3-Aminophenyl)-3-[3-methyl-3-(pyridin-4-yl)propyl]-1,8-naphthyridin-2(1H)-one 1-(3-Aminophenyl)-3-[3-methyl-3-(1-oxypyridin-4-yl)propyl]-1,8-naphthyridin-2(1H)-one 1-(3-Dimethylaminophenyl)-3-[3-methyl-3-(pyridin-4-yl)propyl]-1,8-naphthyridin-2(1H)-one 1-(3-Carbamoylaminophenyl)-3-[3-methyl-3-(pyridin-4-yl)propyl]-1,8-naphthyridin-2(1H)-one 1-(3-Nitrophenyl)-3-[3-oxo-3-(pyridin-4-yl)propyl]-1,8-naphthyridin-2(1H)-one 1-(3-Nitrophenyl)-3-[3-oxo-3-(1-oxypyridin-4-yl)propyl]-1,8-naphthyridin-2(1H)-one 1-(3-Aminophenyl)-3-[3-oxo-3-(pyridin-4-yl)propyl]-1,8-naphthyridin-2(1H)-one 1-(3-Aminophenyl)-3-[3-oxo-3-(1-oxypyridin-4-yl)propyl]-1,8-naphthyridin-2(1H)-one 1-(3-Nitrophenyl)-3-[3-hydroxy-3-(pyridin-4-yl)propyl]-1,8-naphthyridin-2(1H)-one 1-(3-Nitrophenyl)-3-[3-hydroxy-3-(1-oxypyridin-4-yl)propyl]-1,8-naphthyridin-2(1H)-one 1-(3-Nitrophenyl)-3-[3-acetyloxy-3-(pyridin-4-yl)propyl]-1,8-naphthyridin-2(1H)-one 1-(3-Aminophenyl)-3-[3-hydroxy-3-(pyridin-4-yl)propyl]-1,8-naphthyridin-2(1H)-one 1-(2,1,3-Benzothiadiazol-4-yl)-3-[3-(pyridin-4-yl)propyl]-1,8-naphthyridin-2(1H)-one 1-(4-Chloro-3-nitrophenyl-3-[3-(pyridin-4-yl)propyl]-1,8-naphthyridin-2(1H)-one 1-(3-Oxy-2,1,3-benzoxadiazol-5-yl)-3-[3-(pyridin-4-yl)propyl]-1,8-naphthyridin-2(1H)-one 1-(2,1,3-Benzoxadiazol-5-yl)-3-[3-(pyridin-4-yl)propyl]-1,8-naphthyridin-2(1H)-one As used herein, "the compound(s) of the present invention" may include salts thereof, hydrates and solvates thereof, a variety of prodrug forms derived from functional groups existing in compound molecules. The prodrugs of the compounds according to the present invention include those compounds which can be transformed in vivo, for example, by metabolic processes, including hydrolysis, oxidation, reduction, trans-esterification, and the like, to yield the parent compounds of the formula (1), etc. Representatives of such prodrugs are ester-, ether-, amide-, alcohol-, and amine- derivatives thereof. Preferred compounds according to the present invention are potently active in the inhibition of PDE IV.

Some of the compounds of the present invention may exist in more than one tautomeric form. This invention extends to all tautomeric forms. The compounds of the instant invention may also contain one or plural asymmetric carbon atoms and thus give rise to optical isomers such as (R)- and (S)-isomers, racemates, diastereoisomers, etc. The present invention includes all such possible isomers, and their racemic and resolved, enantiomerically pure forms, as well as all mixtures thereof. The compounds of the invention may be isolated in the form of hydrates, solvates with, for example, ethanol and the like, and a variety of crystalline substances.

The present invention also encompasses pharmaceutically acceptable salts of the naphthyridine derivative having the formula (1). Such salts include those formed from any of medically or pharmaceutically utilizable non-toxic or low toxic inorganic or organic acids. Examples of the salts are hydrochloride, hydrobromate, sulfate, acetate, propionate, citrate, succinate, tartrate, methanesulfonate, p-toluenesulfonate, etc.

The compounds of the present invention can be prepared by one of various routes. For instance, the compounds of the formula (1) can be prepared by one of the following schemes or modifications thereof:

1) The compounds of the formula (1) wherein A is methylene or lower alkylmethylene can be prepared, for example, according to the following scheme (I).

Scheme (I)

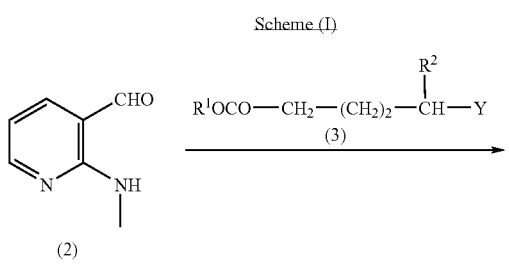

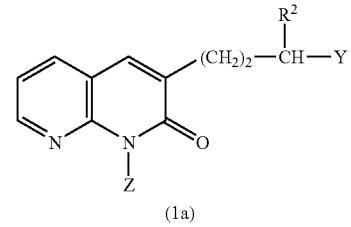

In the aforementioned Scheme, the compounds of the formula (1a) wherein $R^2$ is hydrogen or lower alkyl, Y and Z, both have the meanings given above can be prepared by condensing a compound of the formula (2) wherein Z has the meaning given above with a compound of the formula (3) wherein $R^1$ is lower alkyl, $R^2$ is hydrogen or lower alkyl, and Y has the meaning given above in the presence of a base.

Bases used in this condensation may include alkali metal amides, alkali metal hydrides, alkyl lithium, aryl lithium, and the like. Examples of the base are lithium diisopropylamide (LDA), sodium bistrimethyl-silylamide, potassium hydride, methyl lithium, phenyl lithium, etc. The reaction can be conducted in the presence of or in the absence of a solvent. When the reaction is conducted in solvents, it is often convenient to use conventional solvents which are free from any adverse action on the reaction. Preferred examples of such solvents are tetrahydrofuran (THF), diethyl ether, methylene chloride, etc. The reaction temperature range is about −80 to 100° C. and preferably about −80° C. to room temperature.

In the aforementioned Scheme (I), the compounds of the formula (2) can be prepared by one of known methods (e.g., JP, A, 62-158281 (1987); JP, A, 62-228076 (1987); etc.) or modifications thereof.

In the aforementioned Scheme (I), the compounds of the formula (2) can be prepared by one step (hereinafter, referred to as "process for the production of intermediates") of reacting 2-bromo-nicotinaldehyde with a compound of the formula:

ZNH$_2$ wherein Z has the same meaning as defined above.

For instance, 2-bromonicotinaldehyde prepared according to SYNTHETIC COMMUNICATIONS, 23 (19): 2727–2730 (1993) is reacted with a compound of the formula:

ZNH$_2$ wherein Z has the same meaning as defined above in the presence of a base, palladium, a ligand, and a solvent to give a compound of the formula (2).

Bases used in this process for the production of intermediates may include cesium carbonate, potassium carbonate, sodium carbonate, potassium t-butoxide, sodium t-butoxide, tripotassium phosphate, etc., preferably cesium carbonate.

The "palladium" used in this process for the production of intermediates may include palladium acetate, tris(dibenzylideneacetone) dipalladium, palladium acetylacetonate, palladium black, palladium on activated carbon, palladium chloride, palladium hydroxide, tetrakis(triphenylphosphine) palladium, etc., preferably palladium acetate, and tris(dibenzylidene-acetone) dipalladium.

Ligands used in this process for the production of intermediates may include 1,3-bis-(diphenylphosphino)-propane, 1,2-bis(diphenylphosphino)ethane, 1,4-bis(diphenylphosphino)butane, 2,2'-bis(diphenylphosphino)-1,1'- binaphthyl or an optically active form thereof, 2,2'-bis (dicyclohexylphosphino)-1,1'-binaphthyl or an optically active form thereof, 2,3-O-isopropylidene-2,3-dihydroxy-1, 4-bis(diphenylphosphino)butane or an optically active form thereof, 4,5-bis[bis(4'-methoxy-3',5'-dimethylphenyl)phosphinomethyl]-2,2-dimethyl-1,3-dioxolane or an optically active form thereof, 2,2'-bis[bis(4'-methoxy-3',5'-dimethylphenyl)phosphino]-1,1'-binaphthyl or an optically active form thereof, triphenylphosphine, tri-o-tolylphosphine, tri-m-tolylphosphine, tri-p-tolylphosphine, tributylphosphine, 1,1'-bis(diphenyl-phosphino)ferrocene, 1,2-bis(diphenylphosphino)benzene, 1,2-bis(diphenylphosphino)ethylene, 1-t-butoxycarbonyl-4-diphenylphosphino-2-diphenylphosphinomethylpyrrolidine or an optically active form thereof, etc., preferably 1,3-bis(diphenylphosphino)propane, 1,2-bis(diphenyl-phosphino)ethane, 2,2'-bis(diphenylphosphino)-1,1'-binaphthyl, etc.

In the aforementioned process for the production of intermediates, the reaction can be conducted in the presence of a solvent. When the reaction is conducted in solvents, it is often convenient to use conventional solvents which are free from any adverse action on the reaction. Preferred examples of such solvents are toluene, tetrahydrofuran (THF), diethyl ether, 1,2-dimethoxyethane, etc., preferably toluene. The reaction may be conducted in the absence of a solvent. The reaction temperature range for the aforementioned process for the production of intermediates is about −80 to 200° C. and preferably room temperature to 150° C.

The aforementioned "process for the production of intermediates" is a novel route for producing compounds of the formula (2), and enables the production of the compounds (2) within a simple step in high yields, as compared to the known methods. In other words, as apparent from Synthetic Example 1 disclosed herein below, the process of Synthetic Example 1a) in accordance with the known method requires 5 steps for producing a compound of the formula (2), specifically 2-(2,1,3-benzothiadiazol-5-ylamino)nicotinaldehyde, from a compound of the formula:

ZNH$_2$ specifically 5-amino-2,1,3-benzothiadiazole, while the aforementioned process for the production of intermediates as disclosed in Synthetic Examples 1b) to d) can employ only a single step with high yields for the production of a compound of the formula (2), specifically 2-(3-nitro-phenylamino)-nicotinaldehyde or others, by reacting a compound of the formula:

ZNH$_2$ specifically 3-nitroaniline, etc. with 2-bromo-nicotinaldehyde.

In the aforementioned Scheme (I), the compounds of the formula (3) can be prepared, for example, by one of the synthetic routes described herein. The disclosures given below illustrate the preparation of compounds of the formula (3) wherein Y is pyridyl. For instance, the compounds of the formula (3) wherein Y is pyridyl can be prepared according to Scheme (II) outlined as follows:

Scheme (II)

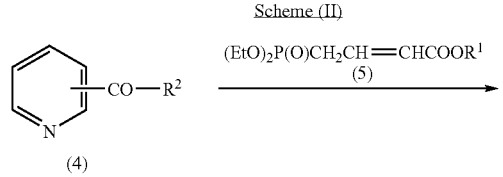

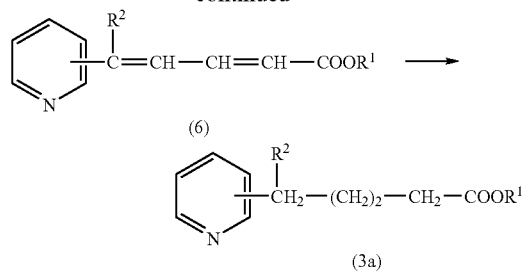

A compound (6) can be prepared by condensing a pyridylcarbonyl compound of the formula (4) wherein R$^2$ is hydrogen or lower alkyl, with a 4-diethylphosphonocrotonic acid lower alkyl ester of the formula (5) wherein R$^1$ is lower alkyl in the presence of a base such as LDA. Next, a compound of the formula (3a) wherein R$^1$ and R$^2$, both have the meanings given above can be prepared by reduction (for example, catalytic reduction) of the compound (6). In this Scheme, the catalytic reduction may be effected generally by hydrogenation in the presence of a suitable catalyst such as palladium on carbon.

The aforementioned Scheme (II) and suitable modifications thereof are adoptable for preparing compounds of the formula (3) wherein Y is a 5- or 6-membered heteroaryl group other than pyridyl.

When the compounds of the formula (1a) wherein Z is amino-substituted phenyl are produced in the aforementioned Scheme (I), they can be prepared according to the following scheme (III):

Scheme (III)

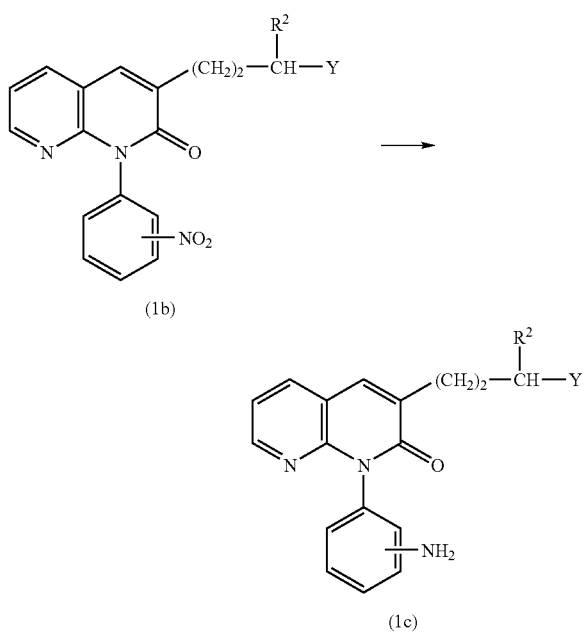

When Z is a phenyl radical substituted with nitro, the compound of the formula (1b) wherein R$^2$ is hydrogen or lower alkyl, and Y has the meaning given above can be reduced to give an amino-substituted phenyl radical (Z)-containing compound of the formula (1c) wherein Y and R$^2$ both have the meanings given above. Embodiments of adoptable reduction conditions in this Scheme include, for example, catalytic reduction wherein catalysts are palladium carried on carbon and the like, systems employing hydrochloric acid and tin chloride, etc.

The compound of the formula (1c) thus prepared is treated, for example, with formalin or a lower alkyl aldehyde (e.g., acetaldehyde, propionaldehyde, butyraldehyde, etc.) under catalytically-reducing conditions to give a mono- or di-lower alkylamino-substituted phenyl radical-containing compound of the present invention wherein said mono- or di-lower alkylamino radical is derived from the amino radical on the phenyl ring. The compound of the formula (1c) is treated, for example, with chlorosulfonyl isocyanate to give a carbamoyl-substituted phenyl radical-containing compound of the present invention wherein said carbamoyl radical is derived from the amino radical on the phenyl ring. The compound of the formula (1c) is treated, for example, with a lower alkyl carboxylic acid (e.g., acetic acid, propionic acid, n-butyric acid, i-butyric acid, etc.) anhydride to give a lower alkylcarbonylamino-substituted phenyl radical-containing compound of the present invention wherein said lower alkylcarbonylamine radical is derived from the amino radical on the phenyl ring.

The aforementioned compounds (1c) and amino nitrogen containing radical-substituted compounds of the present invention wherein said amino nitrogen containing radical is derived from its amino radical are excellently in vivo stable in blood when administered, as compared with the starting nitro-substituted phenyl radical-containing compounds (1b). Therefore, it can be said that the compounds (1c) and amino nitrogen containing radical-substituted compounds have more desired properties in view of therapeutic drugs.

2) Among the compounds of the formula (1) wherein A is carbonyl, hydroxymethylene or lower alkylcarbonyloxymethylene, the compounds of the formula (1) wherein A is carbonyl can be prepared, for example, according to the following scheme (IV):

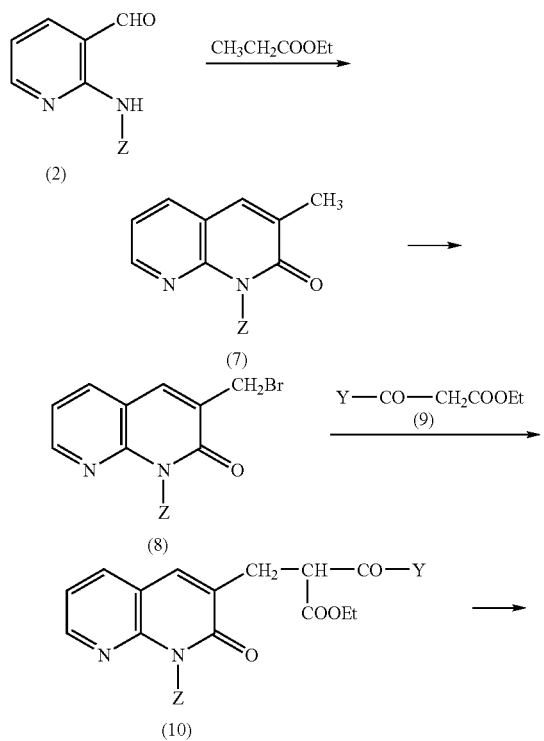

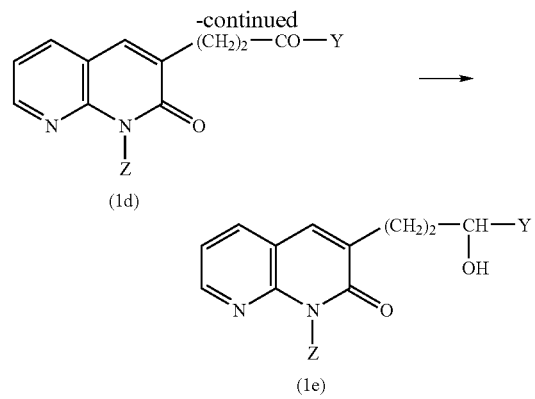

The compound of the formula (2) wherein Z has the meaning given above is condensed with ethyl propionate in the presence of a base in an operating fashion similar to in the aforementioned scheme (I) to give a compound of the formula (7) wherein Z has the meaning given above, which is then brominated with N-bromosuccinimide (NBS), etc. to give a compound of the formula (8) wherein Z has the meaning given. Next, the compound (8) is condensed with a ketocarboxylic acid ethyl ester compound of the formula (9) wherein Y has the meaning given above in the presence of a suitable base (e.g., LDA, sodium bis(trimethylsilyl) amide, sodium hydride, methyl lithium, phenyl lithium, etc.) to give a compound of the formula (10) wherein Y and Z have the meanings given above, which is hydrolyzed with aqueous dilute hydrochloric acid, etc., and then decarboxylated to give a carbonyl (A)-containing compound of the formula (1d) wherein Y and Z have the meanings given above.

The compound of the formula (1d) prepared according to the aforementioned scheme (IV) can be reduced with a suitable reducing agent such as sodium borohydride to give a hydroxymethylene (A)-containing compound of the formula (1e) wherein Y and Z have the meanings given above.

A lower alkylcarbonyloxymethylene (A)-containing compound (1) of the present invention wherein Y and Z have the meanings given above can be prepared by reacting a hydroxy radical on the aforementioned compound (1e), for example, with a lower alkylcarboxylic acid (e.g., acetic acid, propionic acid, n-butyric acid, i-butyric acid, etc.) anhydride.

The compounds of the present invention are potent inhibitors of PDE IV. The compounds of the present invention are thus of use in the prophylaxis and treatment of diseases and abnormal states related to PDE IV actions. In particular, the compounds of the present invention are effective as prophylactic or therapeutic agents for diseases and conditions associated with an abnormal enzymatic or catalytic activity of PDE IV. The compounds of the present invention are valuable as prophylactic or therapeutic agents or drugs for especially the prophylaxis and treatment of:

(1) respiratory diseases, including, for example, bronchial asthma (including chronic bronchial asthma and atopic asthma), acute bronchitis, chronic bronchitis, asthmatic bronchitis, pneumonic diseases, pulmonary emphysema, chronic obstructive pulmonary disease (COPD), acute respiratory distress syndrome (ARDS), and the like;

(2) inflammatory diseases, including, for example, atopic dermatitis, conjunctivitis, urticaria, acquired immunodeficiency syndrome (AIDS), keloid formation, rhinitis, iridocyclitis, gingivitis, periodontitis,. dentoalveolitis, gastritis, ulcerative colitis, Crohn's disease, gastrointestinal ulcer, esophagitis, myositis, encephalitis (such as myasthenia gravis, multiple sclerosis and neuritis), hepatitis, scar tissue formation, nephritis (including proliferative nephritis), peritonitis, pleurisy, scleritis, scleroderma, scalds or burns, and the like;
(3) systemic or local joint diseases, including, for example, osteoarthritis, gouty arthritis, rheumatoid arthritis, malignant rheumatism, psoriatic arthritis, and the like;
(4) inflammatory conditions associated with organ transplantation, etc., including, for example, reperfusion injury, graft versus host reaction, and the like;
(5) diseases or symptoms related to urination, including, for example, diabetes insipidus, urethritis, urinary incontinence, cystitis, irritable bladder, neurogenic bladder, uremia, uriniferous tubular disorder, pollakiuria, ischuria, and the like;
(6) diseases or abnormal conditions related to, for example, tumor necrosis factor (TNF) (TNF-α, etc.) and other cytokines (for example, IL-1, IL-4, IL-6, etc.), including psoriasis, rheumatoid arthritis, ulcerative colitis, Crohn's disease, septicemia, septic shock, endotoxic shock, gram-negative bacillus sepsis, toxic shock syndrome, nephritis, hepatitis, infection (induced by bacteria and viruses), circulatory failure (heart failure, arteriosclerosis, myocardial infarction, cerebral apoplexy), and the like;
(7) proliferative diseases, including, for example, malignant tumors, leukemia, proliferative dermal diseases (keratosis and various types of dermatitides), connective tissue diseases and the like;
(8) diseases related to nervous function abnormality, including, for example, impaired learning, memory and recognition associated with neurodegenerative disorders such as Alzheimer's disease and Parkinson's disease, multiple lateral sclerosis, senile dementia, amyotrophic lateral sclerosis, acute demyelinating neuritis, muscular dystrophy, and the like;
(9) diseases related to abnormality of mental functions, including, for example, manic-depressive psychosis, schizoid, anxiety, panic, and the like;
(10) diseases demanding protection of nerves and cells, including, for example, cardiac arrest, spinal cord injury, intermittent claudication, ischemic diseases (including angina pectoris, cardiac infarction, cerebral apoplexy, head injury, etc.) and the like;
(11) endocrine diseases, including not only diabetes but also diabetic retinopathy, diabetic nephropathy, diabetic neurosis, amyloidosis, pancreatitis, thyroiditis, obesity, prostatomegaly, and the like;
(12) autoimmune diseases, including, for example, systemic lupus erythematosus (SLE), atrophic gastritis, thyroid diseases, glomerular nephritis, orchitis, adrenal diseases, hemolytic anemia, oophoritis, and the like;
(13) cardiovascular diseases, including, for example, hypertension, angina pectoris, heart failure, myocarditis, external epicarditis, endocarditis, valvulitis, and the like;
(14) vessel and blood system diseases, including, for example, angiitis, aneurysm, endoangiosis, thromboangiitis, granulomatosis, cerebrovascular angiitis, arteriosclerosis, periangitis, leukopenia, thrombocytopenia, Boeck's sarcoid, and the like;
(15) diseases related to immune reactions or allergic responses, including, for example, contact dermatitis, serum sickness, drug allergy, Goodpasture's syndrome, lymphoma, rheumatic fever, AIDS, anaphylactic shock and the like; and
(16) other diseases, disorders or abnormal states, including, for example, glaucoma, spastic paralysis, impotence, diseases or illness accompanied with pain (contusion, headache, etc.), neck-shoulder-arm syndrome, nephropathy, renal insufficiency, hepatic insufficiency, obesity, infertility, etc.

It is known that the aforementioned diseases and abnormal conditions would be related to an activity of PDE IV.

Particularly, the compounds of the present invention act as prophylactic and/or therapeutic drugs for:
(i) respiratory diseases (such as bronchial asthma including chronic bronchial asthma and atopic asthma; acute bronchitis; chronic bronchitis; asthmatic bronchitis; pneumonic diseases; pulmonary emphysema; chronic obstructive pulmonary disease (COPD); acute respiratory distress syndrome (ARDS); etc.); and
(ii) atopic dermatitis; conjunctivitis; urticaria; acquired immunodeficiency syndrome (AIDS); keloid formation; rhinitis; iridocyclitis; gingivitis; periodontitis; dentoalveolitis; gastritis; ulcerative colitis; Crohn's disease; gastrointestinal ulcer; esophagitis; myositis; encephalitis (such as myasthenia gravis, multiple sclerosis and neuritis); hepatitis; scar tissue formation; nephritis including proliferative nephritis; peritonitis; pleurisy; scleritis; scleroderma; scalds or burns; etc.

Among them, the compounds of the present invention are most preferably effective as prophylactic and/or therapeutic drugs for bronchial asthma.

It is also verified that the compounds of the present invention are significantly less emetogenic than the prior art PDE IV inhibitors. In other words, as illustrated herein below in assay examples, the prior art PDE IV inhibitors have a slight difference between their pharmacologically-effective dose (such as anti-asthmatic dose) and their emetogenic dose, or raise an emetic action at a less dose than they exert a pharmaceutical action, etc., whereby it is anxious to limit their clinical applications, while the compounds of the present invention have much more higher dose levels for emetic action than for pharmacological action and extremely advantageous in view of safety.

Thus, the present invention encompasses pharmaceutical compositions comprising an effective amount of at least one member selected from the above-defined compounds (1) and pharmaceutically acceptable salts thereof, and not only inhibitors of PDE IV but also anti-asthmatic agents.

As aforementioned, since PDE IV is predominantly in vivo located in airway smooth muscle cells and inflammatory cells, the compounds of the present invention inhibit PDE IV in these cells, thereby exerting a bronchodilator action via relaxing airway smooth muscles, together with an anti-inflammatory action through suppressing inflammatory cell activation. Hence, the compounds of the present invention are widely effective in ameliorating a variety of undesirable responses and symptoms raised with regard to asthma.

The following disclosure is to illustrate an anti-asthmatic efficacy of the compounds of the present invention in detail:

It is known that a series of responses, such as an immediate asthmatic response, a delayed asthmatic response, and a hypersensitive airway response, are induced when an asthmatic patient inhales antigens which cause the disease.

First, the immediate asthmatic response that begins immediately after inhalation of antigens is a typical airway smooth muscle constrictive reaction induced by chemical mediators (including histamine, leukotrienes, etc.) which are released from mast cells as a result of antigen-antibody interactions. Later the delayed asthmatic response is observed, which occurs within 4 to 24 hours after the inhalation of antigens. For its pathological states, an infiltration of inflammatory cells into lung tissues, airway mucosa edema, etc. are observed. Thereafter, the hypersensitive airway response is further elicited, which occurs within 1 to 14 days after the inhalation of antigens and is a state wherein the airway reactivity is increased. In such a stage, even quite mild stimuli lead to constriction of the airway and occurrence of serious airway obstruction.

As aforementioned, various responses and symptoms appear in asthma. The compounds of the present invention can exert an excellent inhibitory and/or ameliorating activity on such responses and symptoms at each stage, relying on their bronchodilator and anti-inflammatory actions based on the inhibition of PDE IV.

Diseases and abnormal states to be targeted by the therapy using the compounds of the present invention include the aforementioned diseases and abnormal conditions, preferably diseases and abnormal conditions accompanied with respiratory dysfunctions and inflammation at the area of bronchus and airway. Embodiments of such diseases include bronchial asthma including chronic bronchial asthma and atopic asthma, acute bronchitis, chronic bronchitis, asthmatic bronchitis, pneumonic diseases, pulmonary emphysema, chronic obstructive pulmonary disease (COPD), acute respiratory distress syndrome (ARDS), and other bronchus and airway inflammatory states, etc.

For patients with the foregoing diseases, disorders, and abnormal states, the compounds of the present invention can be used independently without any additives, but preferably in admixture with any of pharmaceutically acceptable additives. The compounds of the present invention may be orally, parenterally (including by injection), topically (including by inhalation) administered as pharmaceutical compositions or formulations. One or more components selected from known pharmaceutical additives (hereinafter also referred to "pharmaceutical ingredient(s)") can be employed in the aforementioned pharmaceutical compositions or formulations for any of administration routes. Embodiments of such known pharmaceutical additives may be suitably selected, according to administration routes and applications of pharmaceutically formulated forms, from components as disclosed in, for example, (1) "Iyakuhin Tenkabutsu Handbook (Handbook of PHARMACEUTICAL EXCIPIENTS)", Maruzen Publishing Company, Japan (1989);. (2) "Iyakuhin Tenkabutsu Jiten (Pharmaceutical Excipient Dictionary)", First Edition, K. K. Yakuji Nippo Sha, Japan (1994); (3) "Iyakuhin Tenkabutsu Jiten Tsuiho (Pharmaceutical Excipient Dictionary, Supplement)", First Edition, K. K. Yakuji Nippo Sha, Japan (1995); and (4) "Yakuzaigaku (Pharmaceutics)", 5th Edition, K. K. Nankodo, Japan (1997).

For oral administration, the aforementioned additives are any pharmaceutical ingredients as long as they are suitable for oral drugs and the intended purposes according to the present invention. Usually, the pharmaceutical additive is selected from conventional pharmaceutical ingredients such as vehicles, binders, disintegrants, lubricants, and coating agents. The oral formulations of the present invention include tablets, capsules, granules, fine granules, powders, syrups., etc. The oral drug includes controlled-release system preparations wherein the in vivo release of the compound of the present invention which is contained as the active ingredient is controlled using any of known pharmaceutical ingredients (for example, immediate-release preparations, sustained-release preparations, etc.).

The aforementioned oral drug may include enteric preparations. In some cases, it is rather preferable that the oral drugs are prepared in the form of such enteric preparations. Such enteric preparations include capsule formulations wherein any of enteric coating agents is contained as an ingredient for their coat, said enteric coating agent being selected from cellulose phthalate, hydroxypropyl methylcellulose phthalate, and methyl methacrylate-methacrylic acid copolymers, etc.

For injection, the additives include pharmaceutical ingredients suitable for aqueous or non-aqueous injections. Usually, the additive is selected from conventional pharmaceutical ingredients such solubilizers, solution adjuvants, suspending agents, buffers (pH regulators), stabilizers and preservatives. In addition, it may be selected from conventional ingredients suitable for preparing powders for injection, which are used in solution or suspension when administered.

When administered topically, for example, via inhalation, etc., the aforementioned additives as used herein include any of pharmaceutical ingredients known in the art, such as solution adjuvants, stabilizers, buffers, suspending agents, emulsifying agents, and preservatives. Embodiments of inhalants include aerosols. Aerosol-producing techniques are any of types including a spraying type wherein active drug ingredients are packed together with propellants such as fluorocarbon alternatives into a sealed container and sprayed, and a nebulizer or atomizer type using a pressured gas, such as carbon dioxide and nitrogen, filled in a container different from that for active drug ingredients.

Desired oral drugs, injections or drugs for topical applications comprising the compound of the present invention in admixture with the aforementioned ingredient can be prepared according to manufacturing methods known per se, for example, those described in The 13th Pharmacopoeia of Japan (JPXIII) or appropriately modified ones.

The pharmaceutical compositions (drugs) of the present invention are administered to mammals, particularly including human. The doses of these compounds or salts thereof are usually about 0.1 to 1,000 mg (per day), preferably about 0.1 to 500 mg (per day) for oral administration; usually about 0.01 to 200 mg (per day), preferably about 0.05 to 100 mg (per day) for injection; and usually about 0.01 to 200 mg (per day), preferably about 0.05 to 100 mg (per day) for topical applications. Specific administration routes and dose levels (including the optimal dose) for any particular patient will be employed depending upon a variety of factors including the patient's conditions (general health, the severity of the particular disease or symptom undergoing therapy, the presence or absence of complications thereof, etc.), the age, sex, body weight, and the like.

EXAMPLES, ETC.

Described below are examples, including assay examples, synthetic examples and formulation examples, of the present invention which are provided only for illustrative purposes, and not to limit the scope of the present invention. All the examples were carried out or can be carried out, unless otherwise disclosed herein specifically, by standard techniques which are well known and conventional to those skilled in the art.

ASSAY EXAMPLES

Described below are examples of pharmacological assays for the efficacy and safety of the compounds (1) of the present invention wherein their protocols and results are provided.

Assay Example 1

PDE IV Inhibition

<Protocol>

The assays for PDE IV activity were conducted according to Nicholson et al. method (Br. J. Pharmacol., 97, 889 (1989)).

PDE IV isozymes as used herein were separated from U937 culture cells by using an anion exchange chromatography. Type IV PDE isozyme was admixed with ethylene glycol (EG) to adjust the final EG concentration to 30%, then stored at −20° C. and diluted when used. The enzymatic activity for PDE IV was measured using cAMP as a substrate.

[$^3$H]-cAMP (962 GBq/mmol; Amersham, 25 μl (100,000 cpm)) was added together with PDE IV isozyme (25 μl ) to an incubation buffer solution with the composition given below to adjust the total volume to 250 μl. Each test compound was dissolved in DMSO to adjust the final concentration to 1% (2.5 μl/tube). Incubation buffer solution (pH7.5):

Tris-HCl (50 mM), magnesium chloride (6 mM), dithiothreitol (2.5 mM), 5-nucleotidase (4 μg/ml), bovine serum albumin (0.23 mg/ml), and cAMP (1 μM).

A mixture of the aforementioned test compound solution and the buffer solution was incubated at 30° C. for 20 minutes. The reaction was quenched by admixing with 1 ml of anion exchange resin slurry (AG1-X8, 200–400 meshes, chloride form; Bio-Rad) to absorb unreacted substrates. After the reaction stopped, the mixture was centrifuged at 800×g for 10 minutes, and the resulting supernatant was collected with vials in 250 μl aliquots. To each vial was added 5 ml of ACS-II (scintillator, Amersham). The radioactivity was measured with a liquid scintillator counter for [$^3$H]-adenosine and set as the PDE IV activity. The % inhibition was calculated for test compounds, and $IC_{50}$ (the concentration of each test compound required for 50% inhibition) was obtained by Probit method. The results are shown in Table 1. Rolipram ((−)-isomer, optical purity: 91% e.e.) and SB207499 (cis-4-cyano-4-[3-(cyclopentyloxy)-4-methoxyphenyl]cyclohexane-1-carboxylic acid; disclosed in J. Med., Chem., 41, 821 (1998), etc.), known as the PDE IV inhibitors in the prior art, were used for the reference compounds in this assay.

TABLE 1

| Test Compounds | Inhibition of PDE IV ($IC_{50}$; μM) |
| --- | --- |
| Example No. 7 | 0.23 |
| Example No. 8 | 0.067 |
| Example No. 11 | 0.070 |
| Example No. 12 | 0.13 |
| Example No. 17 | 0.45 |
| Rolipram | 0.17 |
| SB207499 | 0.030 |

<Conclusion>

As seen in Table 1, it has been verified that the compounds of the present invention inhibit potently PDE IV.

Assay Example 2

Inhibition of Antigen-Induced Immediate Asthmatic Response (Anti-Asthmatic Action)

<Protocol>

(1) Active Sensitization of Guinea Pigs

Male Hartley outbred guinea pigs were sensitized by administering intraperitoneally physiological saline (0.5 ml) containing ovalbumin (1 mg, antigen) and 5×10$^9$ inactivated *Bordetella pertussis* dead cells (adjuvant). Eleven to thirteen days after the first sensitization, 0.05 ml of an ovalbumin solution (1 mg/ml) (ovalbumin is dissolved in physiological saline) was administered to the lateroabdominal region of each guinea pig intracutaneously. An establishment of sensitization was checked relying on cutaneous reaction. Only guinea pigs wherein significant reddening responses occurred 5 to 10 minutes later were employed in the next measurement test for airway resistance.

(2) Measurement for Airway Resistance in Actively Sensitized-Guinea Pigs

The guinea pigs (3 animals per group) actively sensitized in the above step (1) were employed to measure for their airway pressure according to Konzett-Rossler method (Arch. Exp. Path. Pharmakol., 195, 71 (1940)).

Thirteen days after the final sensitization, guinea pigs fasted overnight, and were on the next day anesthetized with a pentobarbital solution (30 mg/1.2 ml/kg, dissolved in physiological saline, intraperitoneal administration). After the guinea pigs were fixed in a supine position, their trachea was incised followed by insertion with one port of a 4-port cannula. Among the remaining 3 ports, 2 ports were connected to an artificial respirator (Model 683, Harvard). The animals were ventilated with 10 ml/kg of air per ventilation at a rate of 60 beats/min via the artificial respirator from the cannula. One port remainder was connected to a respiratory amplifier (AR-601G, Nihon Kohden, Japan) via an airflow resistance tube (TV-241T, Nihon Kohden, Japan) and a differential pressure transducer (TP-602T, Nihon Kohden, Japan) connected with a control box (RY-111S, Nihon Kohden, Japan). From a catheter inserted into a left carotid artery, blood pressures were monitored with a blood pressure measurement unit (AP641G, NEC Corp., Japan) via a blood pressure transducer (TP-300T, Nihon Kohden, Japan), and heart rates were recorded on a thermal recorder (WT-685G, Nihon Kohden, Japan), relying on blood pressure pulse waves after being led to a cardiograph unit (AT601G, Nihon Kohden, Japan).

After airway pressure became stable, an ovalbumin solution. (1 mg/ml, dissolved in physiological saline) was administered at a dose of 1 ml/kg via a tube with which the right jugular vein of guinea pigs was cannulated. Each area under airway pressure-time curve (AUC) was obtained by measuring amplitudes of the airway pressure prior to the antigen-challenge, 1, 2, 3, 4, 5, 10, 15 and 20 minutes post-challenge, and each percent increase (%) in airway resistance was further calculated according to the following equation:

$$\text{Percent Increase in Airway Resistance } (\%) = \left[ \frac{AUC \text{ for 20 min after Antigen-Challenge}}{\text{Basal Respiratory Pressure} \cdot AUC \text{ for 20 min after Antigen-Challenge}} - 1 \right] \times 100$$

Each test compound was suspended in 0.5% CMC—Na solution and administered orally with an oral sound at a dose of 0.03 to 20 mg/2 ml/kg 60 minutes prior to the antigen-challenge. Control groups received only 0.5% CMC—Na solution in an equivalent amount. The pentobarbital-anesthetization and tracheal incision were conducted 30 minutes prior to the antigen-challenge.

Each percent reduction of increase in airway resistance (each test compound-administered group versus control group) was calculated according to the equation given below. $ED_{50}$ was obtained by Probit method. The results are shown in Table 2. Rolipram and SB207499 as described in Assay Example 1 were used for the reference compounds in this assay.

$$\text{Percent Increase (\%) in Airway Resistance} = 100 - \left( \frac{\text{Percent Increase in Airway Resistance (Test Compound-Administered Group)}}{\text{Percent Increase in Airway Resistance (Control Group)}} \right) \times 100$$

TABLE 2

| Test Compounds | Inhibition of Asthmatic response $ED_{50}$: mg/kg orally |
|---|---|
| Example No. 7 | 1.1 |
| Example No. 8 | 1.2 |
| Example No. 11 | 0.12 |
| Example No. 12 | 0.21 |
| Example No. 17 | 0.71 |
| Example No. 19 | 0.38 |
| Rolipram | 0.51 |
| SB207499 | 20 |

<Conclusion>

As seen in Table 2, it has been verified that the compounds of the present invention exert an excellent inhibitory action on antigen-induced immediate asthmatic responses.

Assay Example 3

Emetic Action

<Protocol>

Male Marshall ferrets (each group consisting of 3 animals) as used herein fasted overnight. On the next day, a suspension of each test compound in 0.5% CMC—Na solution was administered orally to the animals. The animals were observed for emesis occurred within 12 hours after the test compound administration. Next, each maximum tolerance dose against emesis was obtained. SB207499 was used for the reference compound in this assay.

<Conclusion>

There is no observation for emetic actions at asthmatic response-inhibitory $ED_{50}$ levels in Assay Example 2 in connection with the instant compounds (Example Nos. 7 & 8 Compounds). After increasing their dose to about 10 times or more, it has been found an elicitation of emetogenic potentials. In contrast, an elicitation of emetic activity has been found for the test reference compound, SB207499, even at a half of the $ED_{50}$ dose.

In conclusion, it can be said that the instant compounds are of less adverse action concerned and safer than this reference compound.

Assay Example 4

Inhibition of TNF-α Production in Galactosamine- or Lipopolysaccharide (LPS)-Stimulation <Protocol>

A suspension of each test compound in 0.5% CMC—Na solution was administered orally to C3H/HeN mice at a dose of 0.10 to 10 mg/kg. One hour later, the animals received intravenously galactosamine at a dose of 800 mg/kg and LPS at a dose 5 μg/kg to raise the induction of TNF-α production. One hour later after the galactosamine- and LPS-administration, amounts of TNF-α in serum samples were measured by ELISA.

<Conclusion>

The above assay has been carried out for Example No. 7 Compound and SB207499. As a result, it has been verified that the former compound has a better inhibitory action on TNF-α production. $ED_{50}$ is 0.45 mg/kg for the former compound and 0.90 mg/kg for the latter, respectively.

Assay Example 5

Toxicology Study

<Protocol>

Each Compound (Example Nos. 7 and 8) was administered orally to ICR mice (7 animals per group) as a test compound. The mice were observed for the time course of their general health conditions and measured for their body weight. Each test compound was suspended in 0.5% CMC—Na solution and given orally to the animal at a dose of 300 mg/10 ml/kg.

<Conclusion>

None of the animals were died in every dose group when the test compounds were administered. No reduction of body weight gains was observed, either. Further, no abnormality was observed for other parameters.

SYNTHETIC EXAMPLES

Described below are Synthetic Examples 1a) to d) for the compounds of the formula (2) and Synthetic Examples 2 to 8 for the compounds of the formula (3).

Synthetic Example 1 a)

2-(2,1,3-Benzothiadiazol-5-ylamino)nicotinaldehyde (1) A mixture of 2-chloronicotinic acid (14.18 g, 90 mmol), 5-amino-2,1,3-benzothiadiazole (27.34 g, 180 mmol; synthesized according to Chem. Abst., 49, 3170a), potassium carbonate (14.41 g, 104 mmol) and cupric oxide (358 mg, 4.5 mmol) was heated at 140° C. for 4 hours. After admixing with water, the mixture was heated while stirring, then cooled to room temperature, and filtered to give a precipitate. After washing with ether, the resultant crude crystal was dissolved in ethanol-water, and filtered while it was hot. The resulting filtrate was acidified by addition of hydrochloric acid and a deposited precipitate was filtered off. The resultant precipitate was washed with water, and dried under reduced pressure to give 2-(2,1,3-benzothiadiazol-5-ylamino)nicotinic acid (14.52 g, 59%).

$^1$H NMR(DMSO-$d_6$)δ: 7.03–7.07(1H, app-dd, J=4.6 Hz, 7.9 Hz), 7.67–7.71(1H, app-dd, J=2.3 Hz, 9.6 Hz), 7.98–8.02(1H, app-d, J=9.9 Hz), 8.33–8.37(1H, app-dd, J=2.0 Hz, 7.9 Hz), 8.57–8.59(1H, app-dd, J=2.0 Hz, 4.9 Hz), 8.94–8.95(1H, app-ddd, J=2.0 Hz), 10.93(1H, brs)

(2) To a suspension of 2-(2,1,3-benzothiadiazol-5-ylamino)nicotinic acid (14.52 g, 53 mmol) and triethylamine (6.48 g, 64 mmol) in acetone (240 ml) was added dropwise chloroacetonitrile (4.83 g, 64 mmol) while stirring, the mixture was heated under reflux overnight, and a deposited insoluble was filtered off while it was hot. The filtrate was evaporated. The resultant residue was then washed successively with saturated aqueous-sodium hydrogen carbonate and water, filtered off, and dried under reduced pressure to give cyanomethyl 2-(2,1,3-benzothiadiazol-5-ylamino)nicotinate (15.54 g, 93%).

$^1$H NMR(CDCl$_3$)δ: 5.02(2H, s), 6.89–6.94(1H, app-dd, J=4.9 Hz, 7.9 Hz), 7.58–7.62(1H, app-dd, J=2.0 Hz, 9.2 Hz), 7.91–7.95(1H, app-d, J=9.2 Hz), 8.31–8.35(1H, app-dd, J=2.0 Hz, 7.9 Hz), 8.56–8.59(1H, app-dd, J=2.0 Hz, 4.6 Hz), 8.91–8.95(1H, app-d, J=2.0 Hz), 10.24(1H, brs).

(3) A mixture of cyanomethyl 2-(2,1,3-benzothiadiazol-5-ylamino)nicotinate (15.54 g, 50 mmol) and triethylamine (1.01 g, 10 mmol) in dry methanol (170 ml) was heated under reflux overnight. After cooling to room temperature, precipitates were collected by filtration, and washed with methanol to give methyl 2-(2,1,3-benzothiadiazol-5-ylamino)nicotinate (11.84 g, 83%).

$^1$H NMR(CDCl$_3$)δ: 3.98(3H, s), 6.85–6.90(1H, app-dd, J=4.6 Hz, 7.9 Hz), 7.57–7.62(1H, app-dd, J=2.0 Hz, 9.2 Hz), 7.88–7.92(1H, app-dd, J=0.7 Hz, 9.2 Hz), 8.30–8.33(1H, app-dd, J=2.0 Hz, 7.9 Hz), 8.50–8.53(1H, app-dd, J=2.0 Hz, 4.6 Hz), 8.95–8.95(1H, app-d, J=1.7 Hz), 10.61(1H, brs).

(4) To a suspension of methyl 2-(2,1,3-benzothiadiazol-5-ylamino)nicotinate (11.84 g, 41 mmol) and sodium borohydride (6.26 g, 165 mmol) in THF (190 ml) was added methanol (15 ml) dropwise under reflux over 30 min and the mixture was stirred for 30 min, and evaporated under reduced pressure. The residue was admixed with water, and extracted with ethyl acetate. The extract was dried over anhydrous magnesium sulfate, evaporated, and dried to give 3-hydroxymethyl-2-(2,1,3-benzothiadiazol-5-ylamino)pyridine (8.02 g, 75%).

$^1$H NMR(DMSO-d$_6$)δ: 4.67(2H, d, J=4.0 Hz), 5.64(1H, t, J=4.3 Hz), 6.95–7.00(1H, app-dd, J=4.9 Hz, 7.3 Hz), 7.68–7.72(1H, m), 7.79–7.83(1H, app-dd, J=2.3 Hz, 9.6 Hz), 7.93–7.97(1H, app-dd, J=0.7 Hz, 9.6 Hz), 8.24–8.27 (1H, app-dd, J=2.0 Hz, 4.9 Hz), 8.59(1H, brs), 8.66–8.68 (1H, app-dd, J=0.7 Hz, 2.3 Hz).

(5) To a suspension of 3-hydroxymethy-2-(2,1,3-benzothiadiazol-5-ylamino)pyridine (8.02 g, 31 mmol) in chloroform (200 ml) was added manganese dioxide (40 g), the mixture was stirred overnight at room temperature, and filtered through celite to remove an insoluble. Evaporation of solvent yielded a residue which was subjected to purification using column chromatography on silica gel to afford a target product, 2-(2,1,3-benzothiadiazol-5-ylamino)nicotinaldehyde (6.09 g, 77%).

$^1$H NMR(CDCl$_3$)δ: 6.99–7.03(1H, app-dd, J=4.6 Hz, 7.6 Hz), 7.61–7.66(1H, app-dd, J=2.0 Hz, 9.2 Hz), 7.91–7.95 (1H, app-d, J=9.2 Hz), 7.96–8.00(1H, app-dd, J=2.0 Hz, 7.6 Hz), 8.55–8.57(1H, app-dd, J=2.0 Hz, 4.6 Hz), 9.01–9.02 (1H, app-d, J=2.0 Hz), 9.95(1H, s), 10.78(1H, brs).

b) 2-(3-nitrophenylamino)nicotinaldehyde

A suspension of 2-bromonicotinaldehyde (2.54 g, 13.6 mmol; synthesized according to SYNTHETIC COMMUNICATIONS, 23(19): 2727–2730 (1993)), 3-nitroaniline (2.26 g, 1.2 eq.), palladium acetate (123 mg, 0.04 eq.), 1,3-bis (diphenyl-phosphino)propane (341 mg, 0.06 eq.), and cesium carbonate (6.22 g, 1.4 eq.) in toluene (30 ml) was stirred at 100° C. for 4 hours under nitrogen atmosphere, and cooled to room temperature, followed by addition of 10% hydrochloric acid (50 ml) and dichloromethane. The mixture was stirred for 1 hr, then diluted with water (50 ml), and extracted with dichloromethane. The extract was dried, and then evaporated. To the residue was added hexane to precipitate crystals, filtered off, washed with hexane, and dried under reduced pressure to afford 2-(3-nitrophenylamino)nicotinaldehyde as a yellow powder (2.75 g, 74%).

$^1$H NMR (CDCl$_3$)δ: 6.96–7.01 (1H, m), 7.47–7.53 (1H, m), 7.90–7.99 (2H, m), 8.50–8.53 (1H, m), 8.92–8.94 (1H, m), 9.33 (1H, s), 10.71 (1H, s).

c)

2-(2,1,3-Benzothiadiazol-4-ylamino)nicotinaldehyde

A suspension of 2-bromonicotinaldehyde (465 mg, 2.5 mmol), 4-aminobenzothiadiazole (454 mg, 3 mmol, 1.2 eq.), palladium acetate (22 mg, 0.1 mmol, 0.04 eq.), 1,3-bis (diphenylphosphino)propane (62 mg, 0.15 mmol, 0.06 eq.), and cesium carbonate (1.14 g, 3.5 mmol, 1.4 eq.) in toluene (10 ml) was stirred at 100° C. for 5 hours, and cooled to room temperature followed by addition of 10% hydrochloric acid (37.5 ml) and dichloromethane. The mixture was stirred for 1 hr, then diluted with water (37.5 ml), and extracted with chloroform. The extract was treated according to conventional techniques, and purified by flash column chromatography to afford 2-(2,1,3-benzothiadiazol-4-ylamino)nicotinaldehyde (556 m, 87%).

$^1$H NMR (CDCl$_3$)δ: 6.98–7.02 (1H, app-dd, J=4.6 Hz, 7.6 Hz), 7.62 (1H, s), 7.63–7.63 (1H, app-d, J=1.0 Hz), 7.98–8.01 (1H, app-dd, J=2.0 Hz, 7.6 Hz), 8.55–8.58 (1H, app-dd, J=2.0 Hz, 4.6 Hz), 8.84–8.91 (1H, m), 10.02 (1H, s), 11.76(1H, brs).

d) 2-(4-chloro-3-nitrophenylamino)nicotinaldehyde

The procedure of Synthetic Example 1b) was repeated using 4-chloro-3-nitroaniline (518 mg, 3 mmol, 1.2 eq.) in place of 3-nitroaniline to obtain 2-(4-chloro-3-nitrophenylamino)nicotinaldehyde (564 m, 81%).

$^1$H NMR(CDCl$_3$)δ: 7.00–7.02(1H, app-dd, J=4.9 Hz, 7.6 Hz), 7.45–7.48(1H, app-d, J=8.9 Hz), 7.72–7.76(1H, app-dd, J=2.6 Hz, 8.9 Hz), 7.95–7.99(1H, app-dd, J=2.0 Hz, 7.6 Hz), 8.47–8.50(1H, app-dd, J=2.0 Hz, 4.6 Hz), 8.74–8.75 (1H, app-d, J=2.6 Hz), 9.92(1H, s), 10.70(1H, brs).

Synthetic Example 2

Ethyl 5-(pyridin-4-yl)pentanoate

A solution of LDA (16.5 ml of 2M solution, 3.5 g, 0.033 mol) in THF (100 ml) was cooled to −78° C. or below (dry ice-methanol bath) under a nitrogen flow and treated dropwise with triethyl 4-phosphonocrotonate (8.6 g, 0.037 mmol) while stirring. The mixture was further stirred for 15 minutes, treated dropwise with isonicotinaldehyde (3.2 g, 0.030 mol), and then stirred at 0° C. for 1.5 hours. Next, the mixture was treated with acetic acid and evaporated. To the residue was added saturated aqueous sodium hydrogen carbonate and the mixture was extracted with ethyl acetate. The extract was treated according to conventional techniques. Evaporation of solvent yielded ethyl 5-(pyridin-3-yl)-2,4-pentadienoate as a crystalline product (3.3 g).

Ethyl 5-(pyridin-3-yl)-2,4-pentadienoate, prepared in the foregoing step, was dissolved in ethanol (50 ml) without purification. To the solution was added 200 mg of 10% palladium on carbon and the mixture was stirred for 19 hours under a hydrogen flow. After the catalyst was filtered off, the filtrate was evaporated to give ethyl 5-(pyridin-4-yl)pentanoate as an oil (3.2 g, 52%).

$^1$H NMR(CDCl$_3$)δ: 1.25(3H, t, J=7.1 Hz), 1.64–1.70(4H, m), 2.33(2H, t, J=6.9 Hz), 2.62(2H, bs), 4.12(2H, q, J=7.1 Hz), 7.10(2H, d, J=6.0 Hz)i 8.48 (2H, d, J=6.0 Hz).

Synthetic Example 3

Ethyl 5-(pyridin-3-yl)pentanoate

The procedure of Synthetic Example 2 was repeated using nicotinaldehyde as the starting material in place of isonicotinaldehyde to obtain ethyl 5-(pyridin-3-yl)pentanoate.

$^1$H NMR(CDCl$_3$)δ: 1.25(3H, t, J=7.1 Hz), 1.64–1.70(4H, m), 2.33(2H, t, J=6.9 Hz), 2.63(2H, t, J=6.9 Hz), 4.12(2H, q, J=7.1 Hz), 7.18–7.23(1H, m), 7.48(1H, d, J=7.9 Hz), 8.42–8.45(2H, m).

Synthetic Example 4

Ethyl 5-(pyridin-2-yl)pentanoate

The procedure of Synthetic Example 2 was repeated using pyridine-2-carbaldehyde as the starting material in place of isonicotinaldehyde to obtain ethyl 5-(pyridin-2-yl)pentanoate.

$^1$H NMR(CDCl$_3$)δ: 1.25(3H, t, J=7.3 Hz), 1.63–1.84(2H, m), 2.34(2H, t, J=7.5 Hz), 2.81(2H, t, J=7.5 Hz), 4.12(2H, q, J=7.3 Hz), 7.07–7.16(2H, m), 7.56–7.62(1H, app-dt, J=2.0 Hz, 7.6 Hz), 8.51–8.53 (1H, m).

Synthetic Example 5

Ethyl 5-(pyrimidin-5-yl)pentanoate

The procedure of Synthetic Example 2 or partial modifications thereof were repeated using pyrimidine-5-carbaldehyde, prepared according to known methods (e.g., SYNTHETIC COMMUNICATIONS, 24, 253–256 (1994)), in place of isonicotinaldehyde to obtain ethyl 5-(pyrimidin-5-yl)pentanoate.

$^1$H NMR(CDCl$_3$)δ: 1.25(3H, t, J=7.3 Hz), 1.66–1.71(4H, m), 2.30–2.38(2H, m), 2.59–2.67(2H, m), 4.13(2H, q, J=7.3 Hz), 8.57(2H, s), 9.07(1H, s).

Synthetic Example 6

Ethyl 5-(pyridazin-3-yl)pentanoate

The procedure of Synthetic Example 2 was repeated using pyridazine-3-carbaldehyde, prepared according to known methods (e.g., Monatosh. Chem., 104, 1372 (1973)), in place of isonicotinaldehyde to obtain ethyl 5-(pyridazin-3-yl)pentanoate.

$^1$H NMR(CDCl$_3$)δ: 1.25(3H, t, J=7.3 Hz), 1.67–1.91(4H, m), 2.37(2H, t, J=7.3 Hz), 3.03(2H, t, J=7.3 Hz), 4.12(2H, q, J=7.3 Hz), 7.35–7.39(1H, app-dd, J=2.0 Hz, 8.6 Hz), 7.41–7.46(1H, app-dd, J=4.9 Hz, 8.6 Hz), 9.06–9.09(1H, app-dd, J=2.0 Hz, 4.9 Hz).

Synthetic Example 7

Ethyl 5-(pyrazin-2-yl)pentanoate

The procedure of Synthetic Example 2 was repeated using pyrazine-2-carbaldehyde, prepared according to known methods (e.g., J. Org. Chem., 28, 1898 (1963)), as the starting material in place of isonicotinaldehyde to obtain ethyl 5-(pyrazin-2-yl)pentanoate.

$^1$H NMR(CDCl$_3$)δ: 1.25(3H, t, J=7.3 Hz), 1.65–1.87(4H, m), 2.35(2H, t, J=7.3 Hz), 2.84(2H, t, J=6.9 Hz), 4.13(2H, q, J=7.3 Hz), 8.40–8.41(1H, app-d, J=2.6 Hz), 8.46–8.47(1H, app-d, J=1.0 Hz), 8.49–8.50(1H, app-dd, J=1.7 Hz, 2.3 Hz).

Synthetic Example 8

Ethyl 5-methyl-5-(pyridin-4-yl)pentanoate

The procedure of Synthetic Example 2 was repeated using 4-acetylpyridine as the starting material in place of isonicotinaldehyde to obtain ethyl 5-methyl-5-(pyridin-4-yl)pentanoate.

$^1$H NMR(CDCl$_3$)δ: 1.24(3H, t, J=7.3 Hz), 1.25(2H, d, J=6.9 Hz), 1.42–1.67(4H, m), 2.27(2H, t, J=7.3 Hz), 2.64–2.77(1H, m), 4.22(2H, q, J=7.3 Hz), 7.11–7.14(2H, app-d, J=5.9 Hz), 8.49–8.52(2H, app-d, J=5.9 Hz).

EXAMPLES

Disclosed herein below are examples which are merely illustrative of the present invention and should not be construed as limiting the scope of the invention. It should be noted that the present invention encompasses various embodiments.

Example 1

1-(2,1,3-Benzothiadiazol-5-yl)-3-[3-(pyridin-4-yl)propyl]-1,8-naphthyridin-2(1H)-one Ethyl 5-(pyridin-4-yl)pentanoate (1.5 eq., prepared in Synthetic Example 2) was dissolved in dry THF. To the solution was added LDA (2M solution, 1.5 eq.) at −78° C. or below in a dry ice-methanol bath under nitrogen atmosphere while stirring and the mixture was stirred for 1 hour. Next, to the reaction mixture was added dropwise a solution of 2-(2,1,3-benzothiadiazol-5-ylamino)-nicotinaldehyde (1.0 eq., prepared in Synthetic Example 1a)) in THF and the resultant mixture was stirred for 2 hours at −78° C. and then continued to stir for 24 hours until it reached room temperature. The reaction mixture was treated with water, and extracted with methylene chloride. The extract was dried, and evaporated. To the residue was added ethyl acetate to form crystals. Thus, 1-(2,1,3-benzothiadiazol-5-yl) -3-[3-(pyridin-4-yl)propyl]-1,8-naphthyridin-2(1H)-one was obtained. The product was purified through flash column chromatography and recrystallization (yield: 43%, mp 193.5–195.5° C./DMF).

$^1$H NMR(CDCl$_3$)δ: 2.03–2.15(2H, m), 2.73–2.83(4H, m), 7.19–7.23(1H, app-dd, 4.6 Hz, 7.9 Hz), 7.24–7.26(2H, m), 7.46–7.50(1H, app-dd, J=2.0 Hz, 9.2 Hz), 7.64(1H, s), 7.90–7.94(1H, app-dd, J=2.0 Hz, 7.9 Hz), 7.99–8.00(1H, app-dd, J=0.7 Hz, 2.0 Hz), 8.15–8.19(1H, app-dd, J=0.7 Hz, 9.2 Hz), 8.38–8.40(1H, app-dd, J=2.0 Hz, 4.6 Hz), 8.51–8.53(2H, app-d, J=5.6 Hz).

Example 2

1-(2,1,3-Benzothiadiazol-5-yl)-3-[3-(pyridin-3-yl)propyl]-1,8-naphthyridin-2(1H)-one The procedure of Example 1 was repeated using 2-(2,1,3-benzothiadiazol-5-ylamino)nicotinaldehyde (1.0 eq., prepared in Synthetic Example 1a)), ethyl 5-(pyridin-3-yl)pentanoate (1.5 eq., prepared in Synthetic Example 3) and LDA (1.5 eq.) to obtain 1-(2,1,3-benzothiadiazol-5-yl)-3-[3-

(pyridin-3-yl)propyl]-1,8-naphthyridin-2(1H)-one (yield, 48%). The product was purified through flash column chromatography and recrystallization (mp 173.5–174.5° C./DMF).

¹H NMR(CDCl₃)δ: 2.02–2.14(2H, m), 2.73–2.83(4H, m), 7.18–7.23(1H, app-dd, J=4.6 Hz,7.9 Hz), 7.27–7.32(1H, app-dd, J=4.9 Hz,7.6 Hz), 7.46–7.50(1H, app-dd, J=2.0 Hz, 9.2 Hz), 7.64(1H, s), 7.66–7.68(1H, app-t, J=2.0 Hz), 7.91–7.94(1H, app-dd, J=2.0 Hz, 7.9 Hz), 7.99–8.00(1H, app-dd, J=0.7 Hz, 2.0 Hz), 8.15–8.18(1H, app-dd, J=1.0 Hz, 9.2 Hz), 8.37–8.40(1H, app-dd, J=2.0 Hz, 4.9 Hz), 8.45–8.48(1H, app-dd, J=1.0 Hz, 4.9 Hz) 8.52–8.52(1H, app-d, J=0.7 Hz).

Example 3

1-(2,1,3-Benzothiadiazol-5-yl)-3-[3-(pyridin-2-yl)propyl]-1,8-naphthyridin-2(1H)-one The procedure of Example 1 was repeated using 2-(2,1,3-benzothiadiazol-5-ylamino)nicotinaldehyde (1.0 eq., prepared in Synthetic Example 1a)), ethyl 5-(pyridin-2-yl)pentanoate (1.5 eq., prepared in Synthetic Example 4) and LDA (1.5 eq.) to obtain 1-(2,1,3-benzothiadiazol-5-yl)-3-[3-(pyridin-2-yl)propyl]-1,8-naphthyridin-2(1H)-one (yield, 27%). The product was purified through flash column chromatography and recrystallization (mp 169.5–170.5° C./DMF).

¹H NMR(CDCl₃)δ: 2.13–2.25(2H, m), 2.79(2H, t, J=7.9 Hz), 2.97(2H, t, J=7.9 Hz), 7.11–7.16(1H, app-ddd, J=1.0 Hz, 4.9 Hz, 7.6 Hz), 7.17–7.22(1H, app-dd, J=4.6 Hz,7.6 Hz), 7.22–7.25(1H, app-d, J=7.9 Hz), 7.46–7.50(1H, app-dd, J=2.0 Hz, 9.2 Hz), 7.60–7.66(1H, app-dt, J=1.7 Hz, 7.6 Hz), 7.69(1H, s), 7.91–7.94(1H, app-dd, J=1.7 Hz, 7.6 Hz), 7.99–8.00(1H, app-dd, J=1.0 Hz, 2.0 Hz), 8.14–8.18(1H, app-dd, J=0.7 Hz, 9.2 Hz), 8.36–8.39(1H, app-dd, J=2.0 Hz, 4.9 Hz), 8.53–8.55(1H, app-ddd, J=1.0 Hz, 2.6 Hz, 4.9 Hz)

Example 4

1-(3-Nitrophenyl)-3-[3-(pyrimidin-5-yl)propyl]-1,8-naphthyridin-2(1H)-one

The procedure of Example 1 was repeated using 2-(3-nitrophenylamino)nicotinaidehyde (1.0 eq., prepared in Synthetic Example 1b) or according to the procedure of Example 3 in JP, A, 62-228076 (1987)), ethyl 5-(pyrimidin-5-yl)pentanoate (1.5 eq., prepared in Synthetic Example 5) and LDA (1.5 eq.) to obtain 1-(3-nitrophenyl)-3-[3-(pyrimidin-5-yl)propyl]-1,8-naphthyridin-2(1H)-one (yield: 6.2%, mp 175–175.5° C./DMF).

¹H NMR(CDCl₃)δ: 2.01–2.13(2H, m), 2.76(4H, t, J=7.9 Hz), 7.19–7.23(1H, app-dd, J=4.9 Hz, 7.9 Hz), 7.63(1H, s), 7.63–7.67(1H, m), 7.72–7.78(1H, app-t, J=7.9 Hz), 7.90–7.93(1H, app-dd, J=2.0 Hz, 7.6 Hz), 8.19–8.21(1H, app-t, J=2.0 Hz), 8.34–8.39(2H, m), 8.63(2H, s), 9.08(1H, s).

Example 5

1-(3-Nitrophenyl)-3-[3-(pyridazin-3-yl)propyl]-1,8-naphthyridin-2(1H)-one

The procedure of Example 1 was repeated using 2-(3-nitrophenylamino)nicotinaldehyde (1.0 eq.), ethyl 5-(pyridazin-3-yl)pentanoate (1.2 eq., prepared in Synthetic Example 6) and LDA (1.2 eq.) to obtain 1-(3-nitrophenyl)-3-[3-(pyridazin-3-yl)propyl]-1,8-naphthyridin-2(1H)-one (yield, 4.9%). The product was purified through flash column chromatography and recrystallization (mp 234–235° C./DMF).

¹H NMR(CDCl₃)δ: 2.21–2.32(2H, m), 2.80(2H, t, J=7.6 Hz), 3.25(2H, t, J=7.6 Hz), 7.20–7.24(1H, app-dd, J=4.6 Hz, 7.6 Hz), 7.62–7.67(3H, m), 7.72–7.78(1H, app-d, J=7.9 Hz), 7.77(1H, s), 7.95–7.98(1H, app-dd, J=2.0 Hz, 7.9 Hz), 8.18–8.20(1H, app-t, J=2.0 Hz), 8.35–8.39(2H, m), 9.12–9.14(1H, app-dd, J=2.6 Hz, 4.3 Hz).

Example 6

1-(3-Nitrophenyl)-3-[3-(pyrazin-2-yl)propyl]-1,8-naphthyridin-2(1H)-one

The procedure of Example 1 was repeated using 2-(3-nitrophenylamino)nicotinaldehyde (1.0 eq.), ethyl 5-(pyrazin-2-yl)pentanoate (1.5 eq., prepared in Synthetic Example 7) and LDA (1.5 eq.) to obtain 1-(3-nitrophenyl)-3-[3-(pyrazin-2-yl)propyl]-1,8-naphthyridin-2(1H)-one (yield, 33%). The product was purified through flash column chromatography and recrystallization (mp 194–195° C./DMF).

¹H NMR(CDCl₃)δ: 2.13–2.25(2H, m), 2.78(2H, t, J=7.3 Hz), 2.96(2H, t, J=7.6 Hz), 7.18–7.23(1H, app-dd, J=4.9 Hz, 7.9 Hz), 7.63–7.67(1H, app-ddd, J=1.3 Hz, 2.0 Hz, 7.9 Hz), 7.66(1H, s), 7.72–7.78(1H, app-t, J=7.9 Hz), 7.89–7.93(1H, app-dd, J=2.0 Hz, 7.6 Hz), 8.19–8.20(1H, app-t, J=2.0 Hz), 8.34–8.38(2H, m), 8.41–8.42(1H, app-d, J=2.3 Hz), 8.50–8.51(2H, m).

Example 7

1-(3-Aminophenyl)-3-[3-(pyridin-4-yl)propyl]-1,8-naphthyridin-2(1H)-one (1) The procedure of Example 1 was repeated using 2-(3-nitrophenylamino)nicotinaldehyde (1.0 eq.), ethyl 5-(pyridin-4-yl)pentanoate (1.5 eq., prepared in Synthetic Example 2) and LDA (1.5 eq.) to obtain 1-(3-nitrophenyl)-3-[3-(pyridin-4-yl)propyl]-1,8-naphthyridin-2(1H)-one (mp 209–210° C./DMF-EtOH).

¹H NMR(CDCl₃)δ: 2.00–2.12(2H, m), 2.70–2.79(4H, m), 7.15–7.23(3H, m), 7.61–7.67(2H, m), 7.75(1H, t, J=7.9 Hz), 7.89–7.93(1H, m), 8.19–8.20(2H, m), 8.34–8.38(2H, m), 8.50(2H, d, J=5.9 Hz).

(2) To a solution of 1-(3-nitrophenyl)-3-[3-(pyridin-4-yl)propyl]-1,8-naphthyridin-2(1H)-one (1.52 g, 3.93 mmol) in acetic acid (40 ml) and methanol (40 ml) mixture was added 10% palladium on carbon (150 mg) and the mixture was stirred under hydrogen atmosphere for 3 hr. After the catalyst was filtered off, the filtrate was evaporated, extracted with chloroform. The extract was treated according to conventional techniques. Evaporation of solvent yielded a residue which was purified by recrystallization from DMF or flash column chromatography to afford 1-(3-aminophenyl)-3-[3-(pyridin-4-yl)propyl]-1,8-naphthyridin-2(1H)-one (1.20 g, 86%, mp 244–246° C. (dec.)/DMF-EtOH).

¹H NMR(DMSO)δ: 1.85–2.00(2H, m), 2.58(2H, t, J=7.6 Hz), 2.71(2H, t, J=7.6 Hz), 5.19(2H, s), 6.29–6.35(2H, m), 6.60–6.64(1H, m), 7.09–7.15(1H, app-t, J=7.8 Hz), 7.23–7.29(3H, m), 7.89(1H, s), 8.13–8.15(1H, app-dd, J=2.2 Hz, 7.6 Hz), 8.35–8.38(1H, app-dd, J=2.2 Hz, 4.6 Hz), 8.44–8.46(2H, app-dd, J=1.6 Hz, 4.3 Hz).

Example 8

1-(3-Aminophenyl)-3-[3-(1-oxypyridin-4-yl)propyl]-1,8-naphthyridin-2(1H)-one To an ice-cooled solution of 1-(3-aminophenyl)-3-[3-(pyridin-4-yl)propyl]-1,8-naphthyridin-2(1H)-one (356 mg, 1 mmol; prepared in Synthetic Example 7) in chloroform (50 ml) was added m-chloro-perbenzoic acid (purity 70%, 250 mg, 1 mmol) while stirring. After warmed to room temperature, the mixture was further stirred for 7 hr. The organic layer was washed with saturated aqueous sodium hydrogen carbonate and water, dried over anhydrous magnesium sulfate, and evaporated to give a residue which was subjected to purification using column chromatography on silica gel. Recrystallization from i-PrOH yielded 1-(3-aminophenyl)-3-[3-(1-oxypyridin-4-yl)propyl]-1,8-naphthyridin-2(1H)-one (90 mg, 24%; mp 246–248° C. (dec.)/i-PrOH).

$^1$H NMR(CDCl$_3$)δ: 1.99–2.09(2H, m), 2.69–2.77(4H, m), 6.55(1H, app-t, J=2.0 Hz), 6.63(1H, app-d, J=7.9 Hz), 6.79(1H, app-dd, J=2.3 Hz, 7.9 Hz), 7.13–7.17(3H, m), 7.35(1H, app-t, J=7.9 Hz), 7.57(1H, s), 7.85(1H, app-dd, J=2.0 Hz, 7.9 Hz), 8.13(2H, app-d, J=6.9 Hz), 8.46(1H, app-dd, J=2.0 Hz, 4.6 Hz.)

Example 9

1-(3-Dimethylaminophenyl)-3-[3-(pyridin-4-yl)propyl]-1,8-naphthyridin-2(1H)-one To a solution of 1-(3-aminophenyl)-3-[3-(pyridin-4-yl)propyl]-1,8-naphthyridin-2(1H)-one (360 mg, 1 mmol; prepared in Synthetic Example 7) in ethanol (80 ml) was added 37% formalin (5 ml) and 10% palladium on carbon (200 mg), and the mixture was subjected to catalytic reduction under a hydrogen flow (hydrogen pressure: 2.2×10$^3$ Torr) for 5 days while stirring. After the catalyst was filtered off, ethanol was distilled off to give a residue which was dissolved in chloroform (50 ml) and extracted with 2N aqueous hydrochloric acid. The extract was neutralized with 60% aqueous sodium hydroxide, and extracted with chloroform (25 ml×2). The organic layer was treated according to conventional techniques to give a residue which was purified by column chromatography on silica gel to afford 1-(3-dimethylaminophenyl)-3-[3-(pyridin-4-yl)propyl]-1,8-naphthyridin-2(1H)-one (200 mg, 52%; mp 124–127° C./AcOEt-n-Hexane).

$^1$H NMR(CDCl$_3$)δ: 2.02–2.14(2H, m), 2.71–2.82(4H, m), 2.97(6H, s), 6.53–6.59 (2H, m), 6.81–6.85(1H, app-dd, J=2.3 Hz, 8.3 Hz), 7.11–7.16(1H, app-dd, J=4.6 Hz, 7.6 Hz), 7.25–7.26(2H, app-d, J=6.3 Hz), 7.39–7.44(1H, app-t, J=7.9 Hz), 7.56(1H, s), 7.83–7.86(1H, app-dd, J=2.0 Hz, 7.6 Hz), 8.45–8.47(1H, app-dd, J=1.7 Hz, 4.6 Hz), 8.50–8.52(2H, app-d, J=6.3 Hz).

Example 10

1-(3-Acetylaminophenyl)-3-[3-(pyridin-4-yl)propyl]-1,8-naphthyridin-2(1H)-one 1-(3-Aminophenyl)-3-[3-(pyridin-4-yl)propyl]-1,8-naphthyridin-2(1H)-one (100 mg, 0.28 mmol; prepared in Synthetic Example 7) was heated in acetic anhydride (0.5 ml) and pyridine (0.5 ml) at 100° C. for 20 min, concentrated, neutralized with saturated aqueous sodium hydrogen carbonate, and extracted with chloroform. The extract was treated according to conventional techniques. Recrystallization from DMF yielded 1-(3-acetylaminophenyl)-3-[3-(pyridin-4-yl)propyl]-1,8-naphthyridin-2(1H)-one (91.3 mg, 82%; mp 200–202° C./DMF).

$^1$H NMR(CDCl$_3$)δ: 2.01(3H, s), 2.04–2.13(2H, m), 2.71–2.81(4H, m), 6.94–6.96(1H, app-d, J=7.3 Hz), 7.15–7.19(1H, app-dd, J=4.6 Hz, 7.8 Hz), 7.21–7.23(2H, app-d, J=5.9 Hz), 7.36–7.46(2H, m), 7.59(1H, s), 7.62(1H, m), 7.86–7.90(1H, app-dd, J=7.8 Hz, 1.6 Hz), 8.30(1H, s), 8.41–8.43(1H, app-dd, 4.6 Hz, 1.6 Hz), 8.49–8.51(2H, app-d, J=5.9 Hz).

Example 11

1-(3-Nitrophenyl)-3-[3-methyl-3-(pyridin-4-yl)propyl]-1,8-naphthyridin-2(1H)-one The procedure of Example 1 was repeated using 2-(3-nitrophenylamino)nicotinaldehyde (1.0 eq.), ethyl 5-methyl-5-(pyridin-4-yl)pentanoate (1.5 eq.; prepared in Synthetic Example 8) and LDA(1.5 eq.) to obtain 1-(3-nitrophenyl)-3-[3-methyl-3-(pyridin-4-yl)propyl]-1,8-naphthyridin-2(1H)-one (yield, 37%). The product was purified through flash column chromatography and recrystallization (mp 154–155° C./DMF).

$^1$H NMR(CDCl$_3$)δ: 1.33(3H, d, J=6.9 Hz), 1.96–2.05(2H, m), 2.48–2.71(2H, m), 2.77–2.90(1H, m), 7.17–7.22(3H, m), 7.54(1H, s), 7.61–7.66(1H, app-ddd, J=1.3 Hz, 2.0 Hz, 7.9 Hz), 7.72–7.78(1H, app-t, J=7.9 Hz), 7.86–7.90(1H, app-dd, J=1.7 Hz, 7.6 Hz), 8.18–8.19(1H, app-t, J=2.0 Hz), 8.34–8.38(2H, m), 8.52–8.54(2H, app-d, J=5.9 Hz).

Example 12

1-(3-nitrophenyl)-3-[3-methyl-3-(1-oxypyridin-4-yl)propyl]-1,8-naphthyridin-2(1H)-one The procedure of Example 8 was repeated using 1-(3-nitrophenyl)-3-[3-methyl-3-(pyridin-4-yl)propyl]-1,8-naphthyridin-2(1H)-one (213 mg, 0.53 mmol; prepared in Example 11) and m-perbenzoic acid (purity 70%, 261 mg) to obtain 1-(3-nitrophenyl)-3-[3-methyl-3-(1-oxypyridin-4-yl)propyl]-1,8-naphthyridin-2(1H)-one (90.7 mg, 41%; mp 182.5–196.5° C.).

$^1$H NMR(CDCl$_3$)δ: 1.33(3H, d, J=6.9 Hz), 1.94–2.02(2H, m), 2.48–2.70(2H, m), 2.81–2.95(1H, m), 7.19–7.24(3H, m), 7.58(1H, s), 7.62–7.66(1H, app-ddd, J=1.0 Hz, 2.0 Hz, 7.9 Hz), 7.73–7.79(1H, app-t, J=7.9 Hz), 7.88–7.92(1H, app-dd, J=1.7 Hz, 7.6 Hz), 8.18–8.19(1H, app-t, J=2.0 Hz), 8.21–8.23(2H, app-d, J=6.9 Hz), 8.35–8.39(2H, m).

Example 13

1-(3-Aminophenyl)-3-[3-methyl-3-(pyridin-4-yl)propyl]-1,8-naphthyridin-2(1H)-one The procedure of Example 7(2) was repeated using 1-(3-nitrophenyl)-3-[3-methyl-3-(pyridin-4-yl)propyl]-1,8-naphthyridin-2(1H)-one (1.19 g, 2.97 mmol; prepared in Example 11) and 10% palladium on carbon (200 mg) to obtain 1-(3-aminophenyl)-3-[3-methyl-3-(pyridin-4-yl)propyl]-1,8-naphthyridin-2(1H)-one (757 mg, 89%). The product was purified through flash column chromatography (mp 83–91° C.).

$^1$H NMR(CDCl$_3$)δ: 1.33(3H, d, J=6.9 Hz), 1.97–2.06(2H, m), 2.47–2.70(2H, m), 2.82–2.90(1H, m), 3.00(2H, br), 6.54–6.56(1H, app-t, J=2.0 Hz), 6.61–6.65(1H, m), 6.77–6.81(1H, app-ddd, J=1.0 Hz, 2.3 Hz, 8.2 Hz), 7.11–7.15(1H, app-dd, J=4.6 Hz, 7.6 Hz), 7.27–7.29(2H, app-d, J=6.3 Hz), 7.31–7.37(1H, app-t, J=7.9 Hz), 7.49(1H, s), 7.80–7.84(1H, app-dd, J=2.0 Hz, 7.9 Hz), 8.43–8.45(1H, app-dd, J=2.0 Hz, 4.6 Hz), 8.52–8.54(2H, app-d, J=5.9 Hz).

Example 14

1-(3-Aminophenyl)-3-[3-methyl-3-(1-oxypyridin-4-yl)propyl]-1,8-naphthyridin-2(1H)-one The procedure of Example 7(2) was repeated using 1-(3-nitrophenyl)-3-[3-methyl-3-(1-oxypyridin-4-yl)propyl]-1,8-naphthyridin-2(1H)-one, prepared in Example 12, was subjected to catalytic reduction using 10% palladium on carbon, processed in the same manner as in Example 7(2) to obtain 1-(3-aminophenyl)-3-[3-methyl-3-(1-oxypyridin-4-yl)propyl]-1,8-naphthyridin-2(1H)-one (yield, 17%). The product was purified through flash column chromatography (mp 164–180° C.).

$^1$H NMR(CDCl$_3$)δ: 1.31(3H, d, J=6.9 Hz), 1.94–2.04(2H, m), 2.48–2.69(2H, m), 2.82–2.89(1H, m), 2.99(2H, br), 6.57(1H, s), 6.63–6.66(1H, app-d, J=7.9 Hz), 6.79–6.82(1H, app-dd, J=1.7 Hz, 7.9 Hz), 7.12–7.16(1H, app-dd, J=4.6 Hz, 7.6 Hz), 7.19–7.22(2H, app-d, J=6.9 Hz), 7.32–7.37(1H, app-t, J=7.9 Hz), 7.52(1H, s), 7.82–7.86(1H, app-dd, J=2.0 Hz, 7.6 Hz), 8.17–8.19(2H, app-d, J=6.9 Hz), 8.43–8.46(1H, app-dd, J=1.6 Hz, 4.6 Hz).

Example 15

1-(3-Dimethylaminophenyl)-3-[3-methyl-3-(pyridin-4-yl)propyl]-1,8-naphthyridin-2(1H)-one The procedure of Example 9 with partial modifications was repeated using of 1-(3-aminophenyl)-3-[3-methyl-3-(pyridin-4-yl)propyl]-1,8-naphthyridin-2(1H)-one (365 mg, 0.99 mmol; prepared in Example 13), formalin (37%, 5 ml) and 10% palladium on carbon (191 mg) to obtain 1-(3-dimethylaminophenyl)-3-[3-methyl-3-(pyridin-4-yl)propyl]-1,8-naphthyridin-2(1H)-one (75 mg, 19%). The product was purified through flash column chromatography and others (mp 148–154° C.).

$^1$H NMR(CDCl$_3$)δ: 1.32(3H, d, J=6.9 Hz), 1.97–2.06 (2H, m), 2.47–2.71(2H, m), 2.81–2.88(1H, m), 2.96(6H, s), 6.53(1H, s), 6.55–6.58(1H, app-d, J=7.6 Hz), 6.80–6.84(1H, app-dd, J=2.3 Hz, 8.2 Hz), 7.10–7.14(1H, app-dd, J=4.6 Hz, 7.9 Hz), 7.25(2H, br), 7.38–7.44(1H, app-t, J=7.9 Hz), 7.49(1H, s), 7.80–7.84(1H, app-dd, J=2.0 Hz, 7.9 Hz), 8.43–8.46(1H, app-dd, J=2.0 Hz, 4.9 Hz), 8.53(2H, br).

Example 16

1-(3-Carbamoylaminophenyl)-3-[3-methyl-3-(pyridin-4-yl)propyl]-1,8-naphthyridin-2(1H)-one To a solution of 1-(3-aminophenyl)-3-[3-methyl-3-(pyridin-4-yl)propyl]-1,8-naphthyridin-2(1H)-one (185 mg, 0.5 mmol; prepared in Example 13) in dichloromethane (5 ml) was added dropwise a solution of chlorosulfonyl isocyanate (78 mg, 0.55 mmol) in dichloromethane (0.5 ml) at room temperature and the mixture was stirred for 1 hr. Next, after addition of water, the mixture was stirred overnight, admixed with saturated aqueous sodium hydrogen carbonate, and extracted with chloroform. The extract was treated according to conventional techniques, and purified by flash column chromatography to afford 1-(3-carbamoyl-aminophenyl)-3-[3-methyl-3-(pyridin-4-yl)propyl]-1,8-naphthyridin-2(1H)-one (62 mg, 30%; mp 186–190° C.).

$^1$H NMR(DMSO-d$_6$)δ: 1.26(3H, d, J=6.9 Hz), 1.87–1.97 (2H, m), 2.32–2.46(2H, m), 2.78–2.86(1H, m), 6.79–6.82 (1H, app-d, J=8.2 Hz), 6.89–6.90(1H, app-t, J=1.7 Hz), 7.21–7.31(6H, m), 7.36–7.42(1H, app-t, J=7.9 Hz), 7.87(1H, s), 8.12–8.16(1H, app-dd, J=1.7 Hz, 7.6 Hz), 8.34–8.37(1H, app-d, J=1.7 Hz, 4.6 Hz), 8.46–8.48(2H, app-d, J=5.6 Hz), 9.71(1H, s).

Example 17

1-(3-Nitrophenyl)-3-[3-oxy-3-(pyridin-4-yl)propyl]-1,8-naphthyridin-2(1H)-one (1) To a solution of 1-(3-nitrophenyl)-3-methyl-1,8-naphthyridin-2(1H)-one (2.39 g, 8.5 mmol; prepared from 2-(3-nitrophenylamino)nicotinaldehyde, ethyl propionate and LDA in the same manner as in Example 1) in benzene (150 ml) was added NBS (1.53 g, 8.6 mmol) and peroxybenzoyl (41 mg) and the mixture was stirred at 80° C. for 5.5 hr. After removal of the solvent, the residue was purified by flash column chromatography to afford 1-(3-nitrophenyl)-3-bromomethyl-1,8-naphthyridin-2(1H)-one (2.3 g, 53%).

$^1$H NMR(CDCl$_3$)δ: 4.56(2H, s), 7.23–7.28(1H, m), 7.66–7.69(1H, m), 7.73–7.79(1H, app-t, J=7.8 Hz), 7.98–8.01(2H, m), 8.20–8.22(1H, app-t, J=1.9 Hz), 8.36–8.40(1H, m), 8.42–8.44(1H, app-dd, J=1.9 Hz, 4.6 Hz).

(2) To an ice-cooled solution of sodium hydride (50 mg, 1.25 mmol) in DMF(2 ml) was added a solution of ethyl 3-oxo-3-(pyridin-4-yl)propionate (245 mg, 1.26 mmol; prepared according to J. Heterocyclic Chem., 21, 1849 (1984)) in DMF (4 ml) under nitrogen atmosphere while stirring, and the mixture was stirred for 30 min, followed by addition of a solution of 1-(3-nitrophenyl)-3-bromomethyl-1,8-naphthyridin-2(1H)-one (450 mg, 1.25 mmol, obtained in the foregoing step (1)) in DMF(16 ml). The mixture was warmed to room temperature, stirred overnight, then admixed with water while ice-cooling, and extracted with chloroform. The extract was treated according to conventional techniques, and purified by flash column chromatography to afford 1-(3-nitrophenyl)-3-[2-ethoxycarbonyl-3-oxo-3-(pyridin-4-yl)propyl]-1,8-naphthyridin-2(1H)-one (454 mg, 85%; mp 72–73° C.).

$^1$H NMR(CDCl$_3$)δ: 1.16(3H, t, J=7.3 Hz), 3.31(2H, d, J=7.6 Hz), 4.07–4.22(2H, m), 5.05(1H, t, J=7.6 Hz), 7.21–7.26(1H, app-dd, J=4.6 Hz, 7.6 Hz), 7.58–7.72(1H, br), 7.51–7.81(1H, app-t, J=8.1 Hz), 7.90(1H, s), 7.95–8.00 (3H, m), 8.12–8.28(1H, br), 8.38–8.42(2H, m), 8.80–8.98 (2H, br).

(3) To 1-(3-nitrophenyl)-3-[2-ethoxycarbonyl-3-oxo-3-(pyridin-4-yl)propyl]-1,8-naphthyridin-2(1H)-one (161 mg, 0.34 mmol, obtained in the foregoing step (2)) was added 10% aqueous hydrochloric acid (12 ml) and the mixture was heated at 70° C. for 5.5 hours, then allowed to stand until it was cooled, neutralized with saturated aqueous sodium hydrogen carbonate, and extracted with chloroform. The extract was treated according to conventional techniques, and evaporated to afford 1-(3-nitrophenyl)-3-[3-oxo-3-(pyridin-4-yl)propyl]-1,8-naphthyridin-2(1H)-one (123 mg, 90%; mp 199.5–201.5° C./DMF).

$^1$H NMR(CDCl$_3$)δ: 3.14(2H, t, J=7.0 Hz), 3.40–3.50(2H, m), 7.20–7.25(1H, app-dd, J=4.6 Hz, 7.8 Hz), 7.63–7.67 (1H, m), 7.73–7.79(1H, app-t, J=8.1 Hz), 7.81–7.83(2H, app-d, J=5.7 Hz), 7.85(1H, s), 7.94–7.97(1H, app-dd, J=2.2 Hz, 8.1 Hz), 8.19–8.21(1H, app-t, J=2.2 Hz), 8.35–8.40(2H, m), 8.80–8.82(2H, app-dd, J=1.6 Hz, 4.6 Hz).

Example 18

1-(3-Nitrophenyl)-3-[3-oxo-3-(1-oxypyridin-4-yl)propyl]-1,8-naphthyridin-2(1H)-one The procedure of Example 8 was repeated using 1-(3-nitrophenyl)-3-[3-oxo-3-(pyridin-4-yl)propyl]-1,8-naphthyridin-2(1H)-one (313 mg, 0.78 mmol; prepared in Example 17) and m-perbenzoic acid (purity 70%, 579 mg, 2.34 mmol) to obtain 1-(3-nitrophenyl)-3-[3-oxo-3-(1-oxypyridin-4-yl)propyl]-1,8-naphthyridin-2(1H)-one (225.6 mg, 70%; mp 242–244° C./DMF).

$^1$H NMR(CDCl$_3$)δ: 3.12(2H, t, J=7.3 Hz), 3.20–3.42(2H, m), 7.21–7.25(1H, app-dd, J=4.9 Hz, 7.6 Hz), 7.63–7.67(1H, m), 7.74–7.80(1H, app-t, J=8.1 Hz), 7.84–7.88(3H, m), 7.94–7.98(1H, app-dd, J=2.2 Hz, 8.1 Hz), 8.19–8.24(3H, m), 8.36–8.40(2H, m)

Example 19

1-(3-Aminophenyl)-3-[3-oxo-3-(1-oxypyridin-4-yl)propyl]-1,8-naphthyridin-2(1H)-one To a solution of 1-(3-nitrophenyl)-3-[3-oxo-3-(1-oxypyridin-4-yl)propyl]-1,8-naphthyridin-2(1H)-one (104 mg, 0.25 mmol; prepared in Example 18) in conc. hydrochloric acid (2 ml) and ethanol (1 ml) mixture was added dropwise a solution of tin chloride.2H$_2$O (520 mg, 5-fold weights) in ethanol (2 ml) while ice-cooling, the mixture was warmed to room temperature, stirred for 4 hr, evaporated to remove ethanol, neutralized with sodium carbonate, and extracted with chloroform. The extract was treated according to conventional techniques, and evaporated to give a residue which was purified by flash column chromatography to afford 1-(3-aminophenyl)-3-[3-oxo-3-(1-oxypyridin-4-yl)propyl]-1,8-naphthyridin-2(1H)-one (34 mg, 35%; mp 244–246° C.).

$^1$H NMR(DMSO)δ: 2.86–2.91(2H, m), 3.34–3.41(2H, m), 5.21(2H, s), 6.31–6.36(2H, m), 6.60–6.64(1H, m), 7.10–7.16(1H, app-t, J=7.8 Hz), 7.25–7.29(1H, app-dd, J=4.6 Hz, 7.8 Hz), 7.94–7.97(3H, m), 8.11–8.15(1H, app-dd, J=7.8 Hz, 1.6 Hz), 8.32–8.35(2H, app-dd, J=1.6 Hz, 4.9 Hz), 8.37–8.39(1H, app-dd, J=1.6 Hz, 4.9 Hz).

Example 20

1-(3-nitrophenyl)-3-[3-hydroxy-3-(pyridin-4-yl)propyl]-1,8-naphthyridin-2(1H)-one To a solution of 1-(3-nitrophenyl)-3-[3-oxo-3-(pyridin-4-yl)propyl]-1,8-naphthyridin-2(1H)-one (1.07 g, 2.7 mmol; prepared in Example 17) in dichloromethane (50 ml) was added sodium borohydride, and the mixture was admixed dropwise with methanol (30 ml) gradually while the reaction was monitored by TLC. After completion of the reaction, the mixture was evaporated, admixed with water, and filtered to give a solid which was dried. Recrystallization from DMF yielded 1-(3-nitrophenyl)-3-[3-hydroxy-3-(pyridin-4-yl)propyl]-1,8-naphthyridin-2(1H)-one (770 mg, 71%; mp 235–236° C./DMF).

$^1$H NMR(DMSO)δ: 1.82–2.08(2H, m), 2.48–2.78(2H, m), 4.56–4.71(1H, m), 5.58(1H, d, J=4.6 Hz), 7.28–7.33(1H, app-dd, J=4.6 Hz, 7.6 Hz), 7.37–7.39(2H, app-d, J=5.9 Hz), 7.82–7.95(3H, m), 8.17–8.21(1H, app-dd, J=7.6 Hz, 1.6 Hz), 8.26(1H, s), 8.31–8.35(2H, m), 8.49–8.52(2H, app-d, J=5.9 Hz).

Example 21

1-(3-Nitrophenyl)-3-[3-hydroxy-3-(1-oxypyridin-4-yl)propyl]-1,8-naphthyridin-2(1H)-one The procedure of Example 8 was repeated using 1-(3-nitrophenyl)-3-[3-hydroxy-3-(pyridin-4-yl)propyl]-1,8-naphthyridin-2(1H)-one (150 mg, 0.4 mmol; prepared in Example 20) and m-perbenzoic acid (purity 70%, 296 mg, 1.2 mmol) to obtain 1-(3-nitrophenyl)-3-[3-hydroxy-3-(1-oxypyridin-4-yl)propyl]-1,8-naphthyridin-2(1H)-one (116 mg, 69%; mp 246–247° C.).

$^1$H NMR(DMSO)δ: 1.91–1.97(2H, m), 2.57–2.70(2H, m), 4.64–4.66(1H, m), 5.62(1H, d, J=4.6 Hz), 7.29–7.33(1H, app-dd, J=4.9 Hz, 7.6 Hz), 7.37–7.40(2H, app-d, J=7.0 Hz), 7.82–7.87(2H,m), 7.94(1H, s), 8.15–8.36(6H,m).

Example 22

1-(3-Nitrophenyl)-3-[3-acetyloxy-3-(pyridin-4-yl)propyl]-1,8-naphthyridin-2(1H)-one A mixture of 1-(3-nitrophenyl)-3-[3-hydroxy-3-(pyridin-4-yl)propyl]-1,8-naphthyridin-2(1H)-one (50 mg, 0.12 mmol; prepared in Example 20) in acetic anhydride (0.2 ml) and pyridine (0.3 ml) was heated at 100° C. for 20 min, concentrated, and extracted with chloroform. The extract was treated according to conventional techniques, concentrated, and then purified by flash column chromatography to afford 1-(3-nitrophenyl)-3-[3-acetyloxy-3-(pyridin-4-yl)propyl]-1,8-naphthyridin-2(1H)-one (55.2 mg, 100%; mp 69–71° C.).

$^1$H NMR(CDCl$_3$)δ: 2.07(3H, s), 2.10–2.30(2H, m), 2.58–2.78(4H, m), 5.75(1H, t, J=6.6 Hz), 7.12–7.16(1H, app-dd, J=4.9 Hz, 7.6 Hz), 7.20–7.22(2H, app-d, J=7.3 Hz), 7.56(1H, s), 7.58(1H, s), 7.64–7.70(1H, app-t, J=7.8 Hz), 7.82–7.86(1H, app-dd, J=1.6 Hz, 7.8 Hz), 8.11–8.12(1H, app-t, J=1.6 Hz), 8.27–8.31(2H, m), 8.50–8.53(2H, app-d, J=7.3 Hz).

Example 23

1-(3-Aminophenyl)-3-[3-hydroxy-3-(pyridin-4-yl)propyl]-1,8-naphthyridin-2(1H)-one The procedure of Example 19 was repeated using 1-(3-nitrophenyl)-3-[3-hydroxy-3-(pyridin-4-yl)propyl]-1,8-naphthyridin-2(1H)-one (400 mg, 0.99 mmol; prepared in Example 20) and tin chloride.2H$_2$O (2 g, 5-fold weights) while ice-cooling to obtain 1-(3-aminophenyl)-3-[3-hydroxy-3-(pyridin-4-yl)propyl]-1,8-naphthyridin-2(1H)-one (240 mg, 65%; mp 209–211° C.).

$^1$H NMR(DMSO)δ: 1.90–1.99(2H, m), 2.57–2.68(2H, m), 4.62–4.68(1H, m), 5.19(2H, s), 5.56(1H, d, J=4.6 Hz), 6.28–6.34(2H, m), 6.60–6.63(1H, m), 7.09–7.15(1H, app-t, J=7.6 Hz), 7.22–7.27(1H, app-dd, J=4.6 Hz, 7.6 Hz), 7.36–7.38(2H, app-d, J=5.9 Hz), 7.86(1H, s), 8.10–8.14(1H, app-dd, J=7.8 Hz, 1.9 Hz), 8.34–8.37(1H, app-dd, J=1.6 Hz, 4.6 Hz), 8.49–8.51(2H, app-dd, J=1.6 Hz, 4.6 Hz).

Example 24

1-(2,1,3-Benzothiadiazol-4-yl)-3-[3-(pyridin-4-yl)propyl]-1,8-naphthyridin-2(1H)-one The procedure of Example 1 was repeated using 2-(2,1,3-benzothiadiazol-4-ylamino)nicotinaldehyde (1.0 eq.; prepared in Synthetic Example 1c)), ethyl 5-(pyridin-4-yl)pentanoate (1.5 eq.; prepared in Synthetic Example 2) and LDA (1.5 eq.) to obtain 1-(2,1,3-benzothiadiazol-4-yl)-3-[3-(pyridin-4-yl)propyl]-1,8-naphthyridin-2(1H)-one (yield 7%). The target product was purified through flash column chromatography and recrystallization, mp 191–192° C./DMF.

$^1$H NMR(CDCl$_3$)δ: 2.01–2.13(2H, m), 2.72–2.78(4H, m), 7.14–7.16(2H, app-d, J=4.9 Hz), 7.15–7.19(1H, m), 7.59–7.62(1H, app-dd, J=1.0 Hz, 7.3 Hz),7.66(1H, s), 7.76–7.82(1H, app-dd, J=7.3 Hz, 8.9 Hz), 7.90–7.93(1H, app-dd, J=1.7 Hz, 7.6 Hz), 8.14–8.17(1H, app-dd, J=1.0 Hz, 8.9 Hz), 8.26–8.29(1H, app-dd, J=1.7 Hz, 4.6 Hz), 8.48–8.50(2H, app-dd, J=1.6 Hz, 4.3 Hz).

Example 25

1-(4-Chloro-3-nitrophenyl)-3-[3-(pyridin-4-yl)propyl]-1,8-naphthyridin-2(1H)-one The procedure of Example 1 was repeated using 2-(4-chloro-3-nitrophenylamino)nicotinaldehyde (1.0 eq.; prepared in Synthetic Example 1d)), ethyl 5-(pyridin-4-yl) pentanoate (1.5 eq.; prepared in Synthetic Example 2) and LDA (1.5 eq.) to obtain 1-(4-chloro-3-nitrophenyl)-3-[3-(pyridin-4-yl)propyl]-1,8-naphthyridin-2(1H)-one (yield 34%). The target product was purified through flash column chromatography and recrystallization, mp 136–137° C./DMF.

$^1$H NMR(CDCl$_3$)δ: 1.99–2.10(2H, m), 2.69–2.78(4H, m), 7.15–7.17(2H, app-dd, J=1.7 Hz, 4.6 Hz), 7.20–7.24(1H, app-dd, J=4.6 Hz, 7.6 Hz), 7.47–7.51(1H, app-dd, J=2.6 Hz, 8.6 Hz), 7.59(1H, s), 7.72–7.75(1H, app-d, J=8.2 Hz), 7.88–7.92(2H, m), 8.37–8.39(1H, app-dd, J=1.7 Hz, 4.6 Hz), 8.49–8.51(2H, app-dd, J=1.7 Hz, 4.6 Hz).

Example 26

1-(3-Oxy-2,1,3-benzoxadiazol-5-yl)-3-[3-(pyridin-4-yl)propyl]-1,8-naphthyridin-2(1H)-one 1-(4-Chloro-3-nitrophenyl)-3-[3-(pyridin-4-yl)propyl]-1,8-naphthyridin-2(1H)-one (210 mg, 0.5 mmol; prepared in Example 25) was dissolved in dimethyl sulfoxide (2 ml) at 70° C., and sodium azide (36 mg, 0.55 mmol) was added. To the mixture was suitably added additional sodium azide (36 mg, 70 mg, and 70 mg) while the reaction was monitored by HPLC, and then dimethyl sulfoxide (1 ml) was added. The reaction mixture was stirred for 1.5 hr. Water was added and the solution was extracted five times with chloroform. The organic layer was washed with saturated aqueous sodium chloride, dried over anhydrous magnesium sulfate, and evaporated to give a residue which was heated in acetic acid (1 ml) under reflux for 40 min. After the solvent was evaporated, saturated aqueous sodium hydrogen carbonate was added. The resultant mixture was extracted five times with chloroform, dried over anhydrous magnesium sulfate, and evaporated to give a residue which was recrystallized from DMF to afford 1-[3-oxy-2,1,3-benzoxadiazol-5-ylamino]-3-[3-(pyridin-4-yl)propyl]-1,8-naphthyridin-2(1H)-one (58 mg, 29%; mp 196–197° C./DMF(decomp.)).

$^1$H NMR(CDCl$_3$)δ: 1.99–2.11(2H, m), 2.70–2.79(4H, m), 7.15–7.17(2H, app-d, J=5.9 Hz), 7.21–7.26(1H, app-dd, J=4.6 Hz, 7.6 Hz), 7.60(1H, s), 7.89–7.93(1H, app-dd, J=1.7 Hz, 7.6 Hz), 8.38–8.41(1H, app-dd, J=1.7 Hz, 4.6 Hz), 8.50–8.52(2H, app-d, J=5.9 Hz), broad peak at 7.0–7.8.

Example 27

1-(2,1,3-Benzoxadiazol-5-yl)-3-[3-(pyridin-4-yl)propyl]-1,8-naphthyridin-2(1H)-one To a solution of 1-(3-oxy-2,1,3-benzoxadiazol-5-yl)-3-[3-(pyridin-4-yl)propyl]-1,8-naphthyridin-2(1H)-one (120 mg; prepared in Example 26) in ethanol (30 ml) was added triphenylphosphine (78.8 mg, 0.3 mmol) and the mixture was heated under reflux for 1 hr, evaporated to give a residue which was purified by flash column chromatography and recrystallization to afford 1-(2,1,3-benzoxadiazol-5-yl)-3-[3-(pyridin-4-yl)propyl]-1,8-naphthyridin-2(1H)-one (53 mg, 46%; mp 192–194° C./DMF).

$^1$H NMR(CDCl$_3$)δ: 2.01–2.12(2H, m), 2.71–2.79(4H, m), 7.15–7.17(2H, app-d, J=5.9 Hz), 7.20–7.28(2H, m), 7.62 (1H, s), 7.84–7.85(1H, m), 7.90–7.94(1H, app-dd, J=2.0 Hz, 7.9 Hz), 7.96–8.00(1H, app-dd, J=0.7 Hz, 9.2 Hz), 8.37–8.40(1H, app-dd, J=1.6 Hz, 4.9 Hz), 8.49–8.52(2H, app-dd, J=1.7 Hz, 4.6 Hz).

FORMULATION EXAMPLES

Formulation Example 1

A formula for one tablet (total amount per tablet: 150 mg) is given below:

| Compound of the present invention | 30 mg |
|---|---|
| Crystalline Cellulose | 90 mg |
| Corn Starch | 28 mg |
| Magnesium Stearate | 2 mg |

The ingredients were formulated into tablets by known methods according to general pharmaceutical rules prescribed in JPXIII.

Formulation Example 2

A formula for one capsule (total amount per capsule: 180 mg) is given below:

| Compound of the present invention | 50 mg |
|---|---|
| Lactose | 100 mg |
| Corn Starch | 28 mg |
| Magnesium Stearate | 2 mg |

The ingredients were formulated into capsules by known methods according to general pharmaceutical rules prescribed in JPXIII.

Formulation Example 3

The compound of the present invention (10 mg) was dissolved in 3 ml of physiological saline. The solution was adjusted to pH 7 with 0.1 N aqueous sodium hydroxide, to which was added physiological saline to make the total volume 5 ml. The resulting solution was dispensed to each ampule, and then subjected to heat sterilization to obtain injections.

Formulation Example 4

To a mixture of the compound of the present invention (1 g), egg yolk lecithin (1.2 g), α-tocopherol (20 mg) and ascorbic acid (33 mg) was added purified water to make the total volume 100 ml. The resulting product was used as a pharmaceutical preparation for aerosols.

INDUSTRIAL APPLICABILITY

The present invention relates to PDE IV inhibitors. The compounds of the present invention possess potent inhibition of PDE IV. The compounds inhibit PDE IV predominantly present in bronchial smooth muscle cells and inflammatory cells, thereby leading to an elevation of cAMP levels in such cells, with the result that it may be expected to achieve relaxation of bronchial smooth muscle and suppression of inflammatory cell activation. Since it is noted that the compounds have a great difference between their pharmacologically-effective dose and their emetogenic dose as compared with the prior art PDE IV inhibitors. The present invention enables the production of safer anti-asthmatics which possess excellent pharmacological properties.

While the present invention has been described specifically in detail with reference to certain embodiments and examples thereof, it would be apparent that it is possible to practice it in other forms. In light of the disclosure, it will be understood that various modifications and variations are within the spirit and scope of the appended claims.

What is claimed is:

1. A compound of the formula (1):

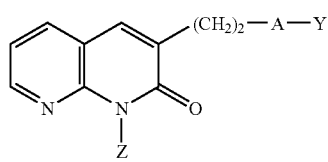

wherein:
A is methylene, lower alkylmethylene, carbonyl, hydroxymethylene or lower alkylcarbonyloxymethylene,
Y is a 5- or 6-membered heteroaryl group containing one or two ring heteroatoms selected from nitrogen, sulfur and oxygen,
Z is
   i) a fused ring in which any of 5- or 6-membered heteroaryl groups is fused to a benzene ring, or
   ii) a phenyl group which may be unsubstituted or optionally substituted with one or more members selected from the group consisting of halogen, cyano, nitro, lower alkylthio, lower alkylsulfinyl, lower alkylsulfonyl, lower alkyl, trifluoromethyl, hydroxyl, lower alkoxy, a carboxylic acid residue, a carbamoyl group, a carboxylic acid lower alkyl ester residue, amino, mono- or di-lower alkylamino, carbamoylamino, and lower alkylcarbonylamino,
   provided that
      when A is methylene, Y is a 5- or 6-membered heteroaryl group selected from the group consisting of pyrrolyl, pyridyl, 1-oxypyridyl, thienyl, furyl, imidazolyl, thiazolyl, and oxazolyl, and Z is a phenyl group which may be unsubstituted or substituted, the substituent on said phenyl group is selected from the group consisting of amino, mono- or di-lower alkylamino, carbamoylamino, and lower alkylcarbonylamino;
or a pharmaceutically acceptable salt thereof.

2. The compound according to claim 1, wherein A is methylene, and Z is a fused ring in which any of 5- or 6-membered heteroaryl groups is fused to a benzene ring; or a pharmaceutically acceptable salt thereof.

3. The compound according to claim 1, wherein A is methylene, and Y is a 6-membered heteroaryl group containing two nitrogen atoms in the ring; or a pharmaceutically acceptable salt thereof.

4. The compound according to claim 1, wherein A is methylene, Y is pyridyl or 1-oxypyridyl, and Z is a substituted phenyl group, wherein the substituent on said phenyl group is selected from the group consisting of amino, mono- or di-lower alkylamino, carbamoylamino, and lower alkylcarbonylamino; or a pharmaceutically acceptable salt thereof.

5. The compound according to claim 1, wherein A is lower alkylmethylene, and Z is a phenyl group which may be unsubstituted or optionally substituted with one or more members selected from the group consisting of halogen, cyano, nitro, lower alkylthio, lower alkylsulfinyl, lower alkylsulfonyl, lower alkyl, trifluoromethyl, hydroxyl, lower alkoxy, a carboxylic acid residue, a carbamoyl group, a carboxylic acid lower alkyl ester residue, amino, mono- or di-lower alkylamino, carbamoylamino, and lower alkylcarbonylamino; or a pharmaceutically acceptable salt thereof.

6. The compound according to claim 1, wherein A is carbonyl, and Z is a phenyl group which may be unsubstituted or optionally substituted with one or more members selected from the group consisting of halogen, cyano, nitro, lower alkylthio, lower alkylsulfinyl, lower alkylsulfonyl, lower alkyl, trifluoromethyl, hydroxyl, lower alkoxy, a carboxylic acid residue, a carbamoyl group, a carboxylic acid lower alkyl ester residue, amino, mono- or di-lower alkylamino, carbamoylamino, and lower alkylcarbonylamino; or a pharmaceutically acceptable salt thereof.

7. The compound according to claim 1, wherein A is hydroxymethylene, and Z is a phenyl group which may be unsubstituted or optionally substituted with one or more members selected from the group consisting of halogen, cyano, nitro, lower alkylthio, lower alkylsulfinyl, lower alkylsulfonyl, lower alkyl, trifluoromethyl, hydroxyl, lower alkoxy, a carboxylic acid residue, a carbamoyl group, a carboxylic acid lower alkyl ester residue, amino, mono- or di-lower alkylamino, carbamoylamino, and lower alkylcarbonylamino; or a pharmaceutically acceptable salt thereof.

8. The compound according to claim 1, wherein A is lower alkylcarbonyloxymethylene, and Z is a phenyl group which may be unsubstituted or optionally substituted with one or more members selected from the group consisting of halogen, cyano, nitro, lower alkylthio, lower alkylsulfinyl, lower alkylsulfonyl, lower alkyl, trifluoromethyl, hydroxyl, lower alkoxy, a carboxylic acid residue, a carbamoyl group, a carboxylic acid lower alkyl ester residue, amino, mono- or di-lower alkylamino, carbamoylamino, and lower alkylcarbonylamino; or a pharmaceutically acceptable salt thereof.

9. The compound according to claim 2, wherein Y is pyridyl or 1-oxypyridyl; or a pharmaceutically acceptable salt thereof.

10. The compound according to claim 3, wherein Z is a phenyl group which may be unsubstituted or optionally substituted with one or more members selected from the group consisting of halogen, cyano, nitro, lower alkylthio, lower alkylsulfinyl, lower alkylsulfonyl, lower alkyl, trifluoromethyl, hydroxyl, lower alkoxy, a carboxylic acid residue, a carbamoyl group, a carboxylic acid lower alkyl ester residue, amino, mono- or di-lower alkylamino, carbamoylamino, and lower alkylcarbonylamino; or a pharmaceutically acceptable salt thereof.

11. The compound according to any of claims 5 to 8, wherein Z is a phenyl group which is substituted with one or more members selected from the group consisting of nitro, amino, mono- or di-lower alkylamino, carbamoylamino, and lower alkylcarbonylamino, and Y is pyridyl or 1-oxypyridyl; or a pharmaceutically acceptable salt thereof.

12. A compound or a pharmaceutically acceptable salt thereof, selected from the group consisting of 1-(3-aminophenyl)-3-[3-(pyridin-4-yl)propyl]-1,8-naphthyridin-2(1H)-one, 1-(3-aminophenyl)-3-[3-(1-oxypyridin-4-yl)propyl]-1,8-naphthyridin-2(1H)-one, 1-(3-nitrophenyl)-3-[3-methyl-3-(pyridin-4-yl)propyl]-1,8-naphthyridin-2(1H)-one, 1-(3-nitrophenyl)-3-[3-methyl-3-(1-oxypyridin-4-yl)propyl]-1,8-naphthyridin-2(1H)-one, 1-(3-nitrophenyl)-3-[3-oxo-3-(pyridin-4-yl)propyl]-1,8-naphthyridin-2(1H)-one, and 1-(3-nitrophenyl)-3-[3-hydroxy-3-(pyridin-4-yl)propyl]-1,8-naphthyridin-2(1H)-one.

13. A pharmaceutical composition which comprises an effective amount of a compound according to claim 1 or 12 or a pharmaceutically acceptable salt thereof in admixture with a pharmaceutically acceptable carrier.

* * * * *